United States Patent
Piers et al.

(10) Patent No.: US 7,365,140 B2
(45) Date of Patent: Apr. 29, 2008

(54) TRANSITION METAL CARBENE COMPLEXES CONTAINING A CATIONIC SUBSTITUENT AS CATALYSTS OF OLEFIN METATHESIS REACTIONS

(75) Inventors: Warren Edward Piers, Calgary (CA); Patricio Eduardo Romero Guajardo, Calgary (CA)

(73) Assignee: UTI Limited Partnership, Calgary, AB (CA)

( * ) Notice: Subject to any disclaimer, the term of this patent is extended or adjusted under 35 U.S.C. 154(b) by 71 days.

(21) Appl. No.: 11/149,722

(22) Filed: Jun. 9, 2005

(65) Prior Publication Data

US 2006/0128912 A1 Jun. 15, 2006

Related U.S. Application Data

(60) Provisional application No. 60/578,200, filed on Jun. 9, 2004.

(51) Int. Cl.
*C08F 4/80* (2006.01)
*C07F 15/00* (2006.01)

(52) U.S. Cl. ............ 526/171; 526/172; 502/155; 502/167; 546/2; 548/101; 544/225

(58) Field of Classification Search ............ 526/171, 526/172; 502/155, 167; 546/2; 548/101; 544/225
See application file for complete search history.

(56) References Cited

U.S. PATENT DOCUMENTS

| | | | |
|---|---|---|---|
| 5,312,940 | A | 5/1994 | Grubbs et al. |
| 5,831,108 | A | 11/1998 | Grubbs et al. |
| 5,969,170 | A | 10/1999 | Grubbs et al. |
| 6,225,488 | B1 | 5/2001 | Mukerjee et al. |
| 6,407,190 | B1 | 6/2002 | Van der Schaaf et al. |
| 6,500,975 | B1 | 12/2002 | Schwab et al. |
| 6,590,048 | B1 | 7/2003 | Furstner |
| 6,803,429 | B2 | 10/2004 | Morgan et al. |

FOREIGN PATENT DOCUMENTS

| | | |
|---|---|---|
| WO | WO 99/51344 | 10/1999 |
| WO | WO 00/58322 | 10/2000 |
| WO | WO 00/71554 | 11/2000 |
| WO | WO 03/029260 | 4/2003 |

OTHER PUBLICATIONS

Audic et al., "An ionic, liquid-supported ruthenium carbene complex: A robust and recyclable catalyst for ring-closing metathesis in ionic liquids," J. Am. Chem. Soc. (2003) 125:9248-9249.
Bassetti et al., "Rate studies and mechanism of ring closing olefin metathesis catalyzed by cationic ruthenium allenylidene arene complexes," Organometallics (2003) 22:4459-4466.
Blackwell et al., "New approaches to olefin cross metathesis," J. Am. Chem. Soc. (2000) 122:58-71.
Cadierno et al., "Efficient synthetic routes to terminal γ-ketoalkynes and unsaturated cyclic carbene complexes based on regio- and diastereoselective nucleophilic addition of enolates on ruthenium (II) indenyl allenylidenes," Organometallics (2001) 20:3175-3189.
Chatterjee et al., "Synthesis of Functionalized Olefins by Cross and Ring-Closing Metatheses," J. Am. Chem. Soc. (2000) 122(15):3783-3784.
Chatterjee et al., "Formyl vinyl C-H activation and allylic oxidation by olefin metathesis," Angew. Chem. Intl. Ed. (2002) 41:3171-3174.
Chatterjee et al., "A general model for selectivity in olefin cross metathesis," J. Am. Chem. Soc. (2003) 125:11360-11370.
Choi et al., "Controlled living ring opening metathesis polymerization by fast initiating ruthenium catalyst," Angew. Chem. Intl. Ed. (2003) 42;1743-1746.
Conrad et al., "The first highly active halide-free ruthenium catalyst for olefin metathesis," Organometallics (2003) 22:3634-3636.
De Clercq et al., "Atom transfer radical polymerization of vinyl monomers mediated by Schiff base ruthenium alkylidene catalysts and the adventitious effect of water in polymerizations with the analogous cationic complexes," Macromol. (2002) 35:8943-8947.
Dinger et al., "High turnover numbers with ruthenium-based metathesis catalysts," Adv. Synth. Catal. (2002) 344:671-677.
Freznel et al., "Ruthenium-based metathesis initiation: development and use in ring opening metathesis polymerization," J. Polymer Sci. (2002) 40:2895-2916.
Furstner et al., "Comparative investigation of ruthenium-based metathesis catalysts bearing N-heterocyclic carbene (NHC) ligands," Chem. Eur. J. (2001) 15:3236-3253.
Garber et al., "Efficient and recyclable monomeric and dendritic Ru-based metathesis catalysts," J. Am. Chem. Soc. (2000) 122:8168-8179.
Grubbs "Handbook of Metathesis," vols. 1, 2 and 3, Wiley VCH, Weinheim, 2003.

(Continued)

*Primary Examiner*—Robert D. Harlan
(74) *Attorney, Agent, or Firm*—Isaac M. Rutenberg; Dianne E. Reed; Mintz, Levin, Cohn, Ferris, Glovsky and Popeo, PC

(57) ABSTRACT

Organometallic complexes suitable as olefin metathesis catalysts are provided. The complexes are Group 8 transition metal carbenes bearing a cationic substituent and having the general structure (I)

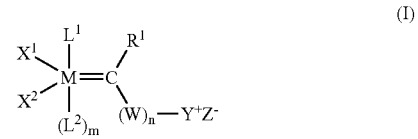

wherein M is a Group 8 transition metal, $L^1$ and $L^2$ are neutral electron donor ligands, $X^1$ and $X^2$ are anionic ligands, m is zero or 1, n is zero or 1, and $R^1$, W, Y, and Z are as defined herein. Methods for synthesizing the complexes are also provided, as are methods for using the complexes as olefin metathesis catalysts.

49 Claims, 6 Drawing Sheets

OTHER PUBLICATIONS

Grubbs et al., "Recent advances in olefin metathesis and its application in organic synthesis," Tetrahedron (1998) 54:4413-4450.

Harrity et al., "Ru-catalyzed rearrangement of styrenyl ethers. Enantioselective synthesis of chromenes through Zr- and Ru-catalyzed processes," J. Am. Chem. Soc. (1997) 119:1488-1489.

Harrity et al., "Chromenes through metal-catalyzed reactions of styrenyl ethers. Mechanism and utility in synthesis," J. Am. Chem. Soc. (1998) 120:2343-2351.

Jung et al., "Cationic vinyl and dicationic carbene ruthenium (II) complexes from a vinylidene (hydrido) precursor," Organometallics (2001) 20:2121-2123.

Jutzi et al., "Synthesis, crystal structure, and application of the oxonium-acid $[H(OEt_2)_2]^+[B(C_6F_5)]$," Organometallics (2000) 19:1442-1444.

Kingsbury et al., "A recyclable ruthenium-based metathesis catalyst," J. Am. Chem. Soc. (1999) 121:791-799.

Love et al., "A practical and highly active ruthenium-based catalyst that effects cross metathesis of acrylonitrile," (2002) Angew. Chem. Intl. Ed. 41:4035-4037.

Love et al., "Synthesis, structure and activity of enhanced initiators for olefin metathesis," J. Am. Chem. Soc. (2003) 125:10103-10109.

Nguyen et al., "Ring-opening metathesis polymerization (ROMP) of norbornene by a group VIII carbene complex in protic media," J. Am. Chem. Soc. (1992) 114:3974-3975.

Pruhs et al., "Preparation, reactivity and structural peculiarities of hydroxyalkyl-functionalized "second generation" ruthenium carbene complexes," Organometallics (2004) 23:280-287.

Romero et al., "Rapidly initiating ruthenium olefin metathesis catalysts," Angew. Chem. Int. Ed. (2004) 43:6161-6165.

Romero et al., "Direct observation of a 14-electron ruthenacyclobutane relevant to olefin metathesis," J. Am. Chem. Soc. (2005) 127:5032-5033.

Sanford et al., "A versatile precursor for the synthesis of ruthenium olefin metathesis catalysts," Organometallics (2001) 20:5314-5318.

Sanford et al., "Mechanism and activity of ruthenium olefin metathesis catalysts," J. Am. Chem. Soc. (2001) 123:6543-6554.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," Organic Letters (1999) 1:953-956.

Schrock "Olefin metathesis reactions catalyzed by molybdenum alkylidenes," Tetrahedron (1999) 55:8141-8153.

Schrock "Living ring-opening metathesis polymerization catalyzed by well characterized transition metal alkylidene complexes," Acc. Chem. Res. (1990) 23:158-165.

Schwab et al., "A series of well-defined metathesis catalysts—synthesis of $[RuCl_2(=CHR')(PR_3)_2]$ and its reactions," Angew. Chem. Intl. Ed. Engl. (1995) 34:2039-2041.

Schwab et al., "Synthesis and applications of $RuCl_2(=CHR')(PR_3)_2$: the influence of the alkylidene moiety on metathesis activity," J. Am. Chem. Soc. (1996) 118:100-110.

Stasko et al., "Molecular structure of the solvated proton in isolated salts. Short, strong, low barrier (SSLB) H-bonds," J. Am. Chem. Soc. (2002) 124:13869-13876.

Trnka et al., "The Development of $L_2X_2Ru=CHR$ Olefin Metathesis Catalysts: An Organometallic Success Story," Acc. Chem. Res. (2001) 34:18-29.

Volland et al., "Synthesis, structure and reactivity of cationic ruthenium (II) carbene complexes with bulky chelating bisphosphines: Design of highly active ring opening metathesis polymerization (ROMP) catalysts," Organometallics (2004) 23:800-816.

Wakamatsu et al., "A new highly efficient ruthenium metathesis catalyst," Angew. Chem. (2002) 114:2509-2511.

Wakamatsu et al., "A highly active and air-stable ruthenium complex for olefin metathesis," Angew. Chem. Int. Ed. (2002) 41:794-796.

Dias et al., "Well-defined ruthenium olefin metathesis catalysts: mechanism and activity," J. Am. Chem. Soc. (1997) 119:3887-3897.

Adhart et al., "Mechanistic studies of olefin metathesis by ruthenium carbene complexes using electrospray ionization tandem mass spectrometry," J. Am. Chem. Soc. (2000) 122:8204-8214.

Adhart et al., "Mechanism and activity of ruthenium olefin metathesis catalysts: the role of ligands and substrates from a theoretical perspective," J. Am .Chem. Soc. (2004) 126:3496-3510.

Cavallo, "Mechanism of ruthenium-catalyzed olefin metathesis reactions from a theoretical perspective," J. Am. Chem. Soc. (2002) 124:8965-8973.

Carlson et al., "The metathesis-facilitated synthesis of terminal ruthenium carbide complexes: a unique carbon atom transfer reaction," J. Am. Chem. Soc. (2002) 124:1580-1581.

TRANSITION METAL CARBENE COMPLEXES CONTAINING A CATIONIC SUBSTITUENT AS CATALYSTS OF OLEFIN METATHESIS REACTIONS

CROSS-REFERENCE TO RELATED APPLICATIONS

This application claims priority under 35 U.S.C. §119(e)(1) to Provisional U.S. Patent Application Ser. No. 60/578,200, filed Jun. 9, 2004, the disclosure of which is incorporated by reference herein.

TECHNICAL FIELD

This invention relates generally to olefin metathesis catalysts, and more particularly pertains to new Group 8 transition metal complexes that are useful as olefin metathesis catalysts. The invention has utility in the fields of catalysis, organic synthesis, and organometallic chemistry.

BACKGROUND OF THE INVENTION

Olefin metathesis catalysis is a powerful technology, which in recent years has received tremendous attention as a versatile method for the formation of carbon-carbon bonds and has numerous applications in organic synthesis and polymer chemistry (R. H. Grubbs, Handbook of Metathesis, Vol. 2 and 3; Wiley VCH, Weinheim, 2003). The family of olefin metathesis reactions includes ring-closing metathesis (RCM), cross metathesis (CM or XMET), ring-opening metathesis polymerization (ROMP), and acyclic diene metathesis polymerization (ADMET). The success of olefin metathesis stems from the development of several well-defined transition metal complexes, such as the Schrock molybdenum catalysts and the Grubbs ruthenium and osmium catalysts (see, e.g., Schrock (1999) *Tetrahedron* 55, 8141-8153; Schrock (1990) *Acc. Chem. Res.* 23, 158-165; Grubbs et al. (1998) *Tetrahedron* 54, 4413-4450; Tmka et al. (2001) *Acc. Chem. Res.* 34, 18-29; Grubbs, *Handbook of Metathesis*, Vol. 1; Wiley VCH, Weinheim, 2003). Following the discovery of these complexes, a significant amount of olefin metathesis research has focused on tuning the ruthenium and osmium carbene catalysts in order to increase their activity, selectivity, and/or stability. The most common strategy has involved the replacement of mono-dentate ligands with other mono-dentate ligands to provide the catalytic complexes with new and useful properties.

The original breakthrough ruthenium catalysts were primarily bisphosphine complexes of the general formula $(PR_3)_2(X)_2M=CHR'$ wherein M is ruthenium (Ru) or osmium (Os), X represents a halogen (e.g., Cl, Br, or I), R represents an alkyl, cycloalkyl, or aryl group (e.g., butyl, cyclohexyl, or phenyl), and R' represents an alkyl, alkenyl, or aryl group (e.g., methyl, $CH=C(CH_3)_2$, phenyl, etc.) (see Nguyen et al. (1992) *J. Am. Chem. Soc.* 1992, 114, 3974-3975; Schwab et al. (1995) *Angew. Chem., Int. Ed.* 34, 2039-2041; Schwab et al. (1996) *J. Am. Chem. Soc.* 118, 100-110). Examples of these types of catalysts are described in U.S. Pat. Nos. 5,312,940, 5,969,170 and 6,111,121 to Grubbs et al. While such complexes are capable of catalyzing a considerable number of olefin metathesis transformations, these bisphosphine complexes can exhibit lower activity than desired and, under certain conditions, can have limited lifetimes.

More recent developments in the field have led to increased activity and stability by replacing one of the phosphine ligands with a bulky N-heterocyclic carbene (NHC) ligand (Scholl et al. (1999) *Organic Letters* 1, 953-956) to give complexes of the general formula $(L)(PR_3)(X)_2Ru=CHR'$, wherein L represents an NHC ligand such as 1,3-dimesitylimidazole-2-ylidene (IMes) and 1,3-dimesityl-4,5-dihydroimidazol-2-ylidene (sIMes), X represents a halogen (e.g., Cl, Br, or I), R represents an alkyl, cycloalkyl, or aryl group (e.g., butyl, cyclohexyl, or phenyl), and R' represents an alkyl, alkenyl, or aryl group (e.g., methyl, $CH=C(CH_3)_2$, phenyl, etc.). Representative structures include complex A (ibid.), complex B (Garber et al. (2000) *J. Am. Chem. Soc.* 122, 8168-8179), and complex C (Sanford et al. (2001) *Organometallics* 20, 5314-5318; Love et al. (2002) *Angew. Chem., Int. Ed.* 41, 4035-4037):

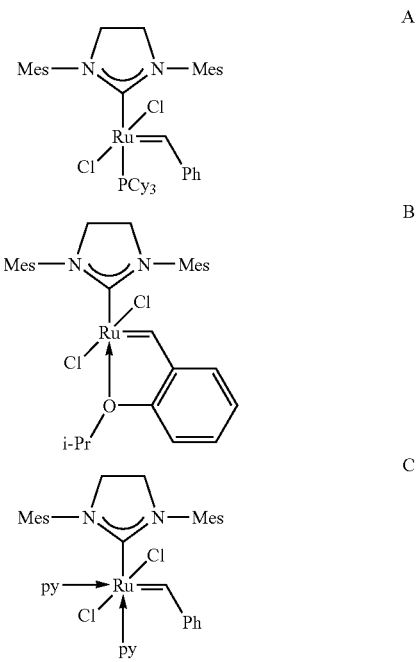

Unlike prior bisphosphine complexes, the various imidazolylidine catalysts effect the efficient formation of trisubstituted and tetrasubstituted olefins through catalytic metathesis. Examples of these types of catalysts are described in PCT publications WO 99/51344 and WO 00/71554. Further examples of the synthesis and reactivity of some of these active ruthenium complexes are reported by Fürstner et al. (2001) *Chem. Eur. J.* 7, No. 15, 3236-3253; Blackwell et al. (2000) *J. Am. Chem. Soc.* 122, 58-71; Chatterjee et al. (2000) *J. Am. Chem. Soc.* 122, 3783-3784; Chatterjee etal. (2000) *Angew. Chem. Int. Ed.* 41, 3171-3174; Chatterjee et al. (2003) *J. Am. Chem. Soc.* 125, 11360-11370. Further tuning of these catalysts led to even higher activity by using bulkier imidazolylidine ligands such as 1,3-bis(2,6-diisopropylphenyl)-4,5-dihydroimidazol-2-ylidenes (Dinger et al. (2002) *Adv. Synth. Catal.* 344, 671-677) or electron deficient phosphine ligands such as fluorinated aryl phosphines (Love et al. (2003) *J. Am. Chem. Soc.* 125, 10103-10109).

Another example of ligand substitution that has led to enhanced catalyst activity is the replacement of the phosphine ligand in the $(L)(PR_3)(X)_2M=CHR'$ complexes with one or two pyridine-type ligands to give compounds of the general formula $(L)(L')_n(X)_2M=CHR'$ wherein n=1 or 2, L represents an imidazolylidine ligand, L' represents a pyridine (Py) or substituted pyridine ligand, X represents a halogen (e.g., Cl, Br, or I), and R¹ represents an alkyl, alkenyl, or aryl group (e.g., methyl, CH=C(CH₃)₂, phenyl, etc.). These pyridine complexes are extremely fast-initiating and catalyze living ring-opening metathesis polymerizations (Choi et al. (2003) *Chem. Int. Ed.* 42, 1743-1746) as well as highly challenging processes such as olefin cross metathesis with acrylonitrile (Love et al. (2002) *Angew. Chem. Int. Ed.* 41, 4035-4037).

Yet another example of mono-dentate ligand substitution is the replacement of the halogen ligands with aryl-oxo ligands, which in one example has led to a catalyst with enhanced activity: $(L)(L')_n(RO)_2Ru=CHR'$ wherein n=1, L represents an imidazolylidine ligand, L' represents a pyridine ligand, R represents a fluorinated aryl group, and R' represents an alkyl, alkenyl, or aryl group (Conrad et al. (2003) *Organometallics* 22, 3634-3636).

A different strategy to tune olefin metathesis catalysts involves linking two of the ligands that are attached to the metal center. Of particular interest are the chelating carbene species reported by Hoveyda and others (Gaber et al. (2000) *J. Am. Chem. Soc.* 122, 8168-8179; Kingsbury et al. (1999) *J. Am. Chem. Soc.* 121, 791-799; Harrity et al. (1997) *J. Am. Chem. Soc.* 119, 1488-1489; Harrity et al. (1998) *J. Am. Chem. Soc.* 120, 2343-2351). These catalysts are exceptionally stable and can be purified by column chromatography in air.

Fewer efforts to differentiate catalyst performance and regulate olefin metathesis reactions have focused on the development of charged ruthenium metal complexes. Several groups have demonstrated cationic compounds of the general type $[(L)(L')(X)Ru=(C)_n=CRR']^+$ (L and L' are any of a variety of neutral electron donors, X is typically halide, and n=0,1,2...). In U.S. Pat. No. 6,590,048, Fürstner teaches the use of cationic vinylidene, allylidene and higher cumulene complexes for a variety of olefin metathesis reactions. In U.S. Pat. No. 6,500,975, Schwab and coworkers describe the use of cationic ruthenium alkylidyne complexes and their use in the metathesis of electron poor olefins. In U.S. Pat. No. 6,225,488, Mukerjee et al. teach the use of cationic (bisallyl) vinylidene complexes of ruthenium or osmium for the ring-opening metathesis polymerization of norbornene derivatives. Other cationic Group 8 metathesis catalysts have been described by Jung et al. (2001) *Organometallics* 20:2121; Cadiemo et al. (2001) *Organometallics* 200:3175; De Clereq et al. (2002) *Macromolecules* 35:8943; Bassetti et al. (2003) 22:4459; Prühs et al. (2004) *Organometallics* 23:280; and Volland et al. (2004) *Organometallics* 23:800. These are typically derived from abstraction of an anionic ligand from the coordination sphere of a neutral metal precursor. Alternatively, a cationic ligand in a neutral complex may be replaced by a neutral ligand resulting in cationic metal complexes. Distinct from the above-described complexes, Audic et al. (2003) *J. Am. Chem. Soc.* 125:9248 makes use of olefin cross metathesis to link an imidazolium salt to the carbene moiety of a Grubbs or a Grubbs-Hoveyda catalyst precursor. The immediate coordination sphere of the resulting complexes remains intentionally unchanged, but the distal imidazolium salt confers solubility to the catalyst precursor in certain ionic liquids. These efforts were directed to the development of ionic liquid "supported" catalysts to facilitate catalyst recycle.

As will be discussed in further detail infra, the root of the lower activities of the some of the Grubbs catalysts, which may be generically denoted as $X_2(L)(L')Ru=C(H)R$, lies in their mode of initiation and the accessibility of the reactive species, the 14-electron alkylidene $X_2(L)Ru=C(H)R$ formed upon reversible dissociation of L'. Most of the improvements to the Grubbs "first generation" catalysts, e.g., $Cl_2(PCy_3)_2Ru=C(H)Ph$ (Cy=cyclohexyl), are modifications that either encourage loss of L' (Love et al. (2003) *J. Am. Chem. Soc.* 125:10103) or reduce the tendency of $Cl_2(L)Ru=C(H)R$ to re-capture the liberated L' (Sanford et al. (2001) *J. Am. Chem. Soc.* 123:6543) which competes with the olefin substrate for the unsaturated metal center in $Cl_2(L)Ru=C(H)R$. Alternatively, Hoveyda had developed a series of catalysts in which L' is a loosely chelating group associated with the carbene ligand that is removed upon the first metathesis event. See Kingsbury et al. (1999) *J. Am. Chem. Soc.* 121:791; Hoveyda (1999) *J. Am. Chem. Soc.* 121:791; and Garber et al. (2000) *J. Am. Chem. Soc.* 122:8168.

Despite these advances there remains a need for olefin metathesis catalysts that are highly active as well as stable to air and moisture, thermally stable, and tolerant of functional groups on the olefin substrates. Ideal catalysts would also be "tunable" with regard to activity, including initiation time and substrate conversion rate.

SUMMARY OF THE INVENTION

The invention is addressed to the aforementioned need in the art, and provides new organometallic complexes useful as catalysts of olefin metathesis reactions. Relative to known olefin metathesis catalysts, the novel catalysts dramatically shorten the latency period of the metathesis reaction, significantly increase the rate at which the reaction occurs, and substantially shorten the time to reaction completion. As such, the complexes of the invention are highly active metathesis catalysts.

In one embodiment, an organometallic complex useful as an olefin metathesis catalyst is provided, the complex having the structure of formula (I)

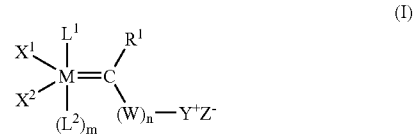

wherein:

M is a Group 8 transition metal;

$L^1$ and $L^2$ are neutral electron donor ligands;

$X^1$ and $X^2$ are anionic ligands;

$R^1$ is hydrogen, $C_1$-$C_{12}$ hydrocarbyl, or substituted $C_1$-$C_{12}$ hydrocarbyl;

W is an optionally substituted and/or heteroatom-containing $C_1$-$C_{20}$ hydrocarbylene linkage;

Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;

$Z^-$ is a negatively charged counterion;

m is zero or 1; and n is zero or 1;

wherein any two or more of $L^1$, $L^2$, $X^1$, $X^2$, $R^1$, W, and Y can be taken together to form a cyclic group.

Exemplary catalysts are those wherein m and n are both zero.

In another embodiment, methods are provided for synthesizing the organometallic complexes of the invention.

One such method involves synthesis of an organometallic complex having the structure of formula (XI)

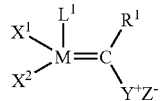
(XI)

wherein M is a Group 8 transition metal, $L^1$ is a neutral electron donor ligand, $X^1$ and $X^2$ are anionic ligands, $R^1$ is hydrogen, $C_1$-$C_{12}$ hydrocarbyl, or substituted $C_1$-$C_{12}$ hydrocarbyl, Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, and $Z^-$ is a negatively charged ion, the method comprising contacting a Group 8 transition metal carbide having the structure (XIII)

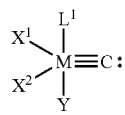
(XIII)

with an ionic reagent of the formula $[R^1]^+[Z]^-$. The $[R^1]^+$ moiety in the ionic reagent is typically hydrogen, and may be associated with a polar solvent (as in $[H(Et_2O)_2][B(C_6F_5)_4]^-$, also referred to as "Jutzi's acid"; see Jutzi et al. (2000) *Organometallics* 19:1442).

The invention also provides a method for synthesizing an organometallic complex having the structure of formula (II)

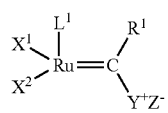
(II)

wherein $L^1$, $X^1$, $X^2$, $R^1$, and Y are as defined previously, with Y preferably being a $C_1$-$C_{12}$ hydrocarbyl-substituted, positively charged Group 15 or Group 16 element, and $Z^-$ is of the formula $B(R^{15})_4^-$ where $R^{15}$ is fluoro, aryl, or perfluorinated aryl, the method comprising:

(a) contacting (i) a ruthenium complex having the structure (XIV)

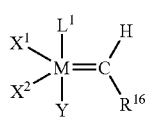
(XIV)

where $R^{16}$ is $C_1$-$C_{20}$ hydrocarbyl, with (ii) a reagent effective to convert the ruthenium complex to the ruthenium carbide (XV)

(XV)

and (b) contacting the ruthenium carbide with a protonating reagent of the formula $[H(OR_2)_2]^+[B(R^{15})_4]^-$ where R is $C_1$-$C_6$ hydrocarbyl.

In a further embodiment, a method is provided for synthesizing an organometallic complex having the structure of formula (XII)

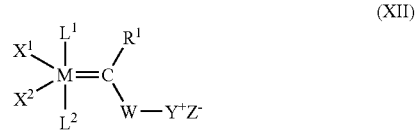
(XII)

wherein M, $L^1$, $X^1$, $X^2$, $R^1$, and Y are as defined previously, W is an optionally substituted and/or heteroatom-containing $C_1$-$C_{20}$ hydrocarbylene linkage, Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, and $Z^-$ is a negatively charged ion, the method comprising contacting an organometallic complex having the structure (XVI)

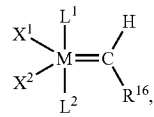
(XVI)

where $R^{16}$ is $C_1$-$C_{20}$ hydrocarbyl, with an ionic reagent having the structure $H_2C=CR^1$—W—$Y^+Z^-$ under conditions effective to enable cross metathesis between the transition metal alkylidene group in the complex and the olefinic moiety in the reagent.

Another such method is provided for synthesizing an organometallic complex of the invention having the structure of formula (VII)

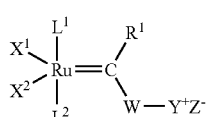
(VII)

wherein $L^1$, $L^2$, $X^1$, $X^2$, $R^1$, W, Y are as defined previously, with W preferably being an optionally substituted $C_1$-$C_{12}$ alkylene linkage and Y preferably being a positively charged Group 15 or Group 16 element substituted with and Z is of the formula $B(R^{15})_4^-$ where $R^{15}$ is fluoro, aryl, or perfluorinated aryl, the method comprising contacting a ruthenium complex having the structure (XVII)

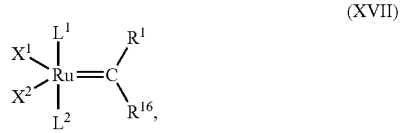

(XVII)

where $R^{16}$ is as defined above, with an ionic reagent having the structure $H_2C=CR^1-W-Y^+Z^-$, under conditions effective to enable cross metathesis between the ruthenium alkylidene group in the complex and the olefinic moiety in the reagent.

In another embodiment, a method is provided for catalyzing an olefin metathesis reaction, comprising contacting at least one olefinic reactant with a catalytically effective amount of an organometallic complex of the invention under reaction conditions effective to enable olefin metathesis. The metathesis reaction may be ring-closing metathesis, cross metathesis, ring-opening metathesis polymerization, or acyclic diene metathesis polymerization.

The invention represents a substantial improvement relative to prior Group 8 transition metal complexes used as olefin metathesis catalysts. Prior such catalysts, including those described in Schrock et al. (1990) *J. Am. Chem. Soc.* 112:3875, Schrock et al. (2003) *Angew. Chem.* 115:4740, Schrock et al. (2003) *Angew. Chem. Int. Ed.* 42:4592, and Trnka et al. (2001) *Acc. Chem. Res.* 34:18, were either highly active but moisture-sensitive and intolerant of polar functional groups (e.g., those described in the Schrock et al. publications) or moisture-insensitive and tolerant of polar functional groups but lacking high activity (e.g., those described by Trnka et al.). By contrast, the present complexes and methods provide all of the foregoing advantages, including high activity, moisture-insensitivity, and tolerance of polar functional groups. In addition, the initiation time and substrate (i.e., olefinic reactant) conversion rate can be tuned as desired by appropriately spacing the distance of the cationic species $[Y]^+$ from the metal center.

Figure 1:
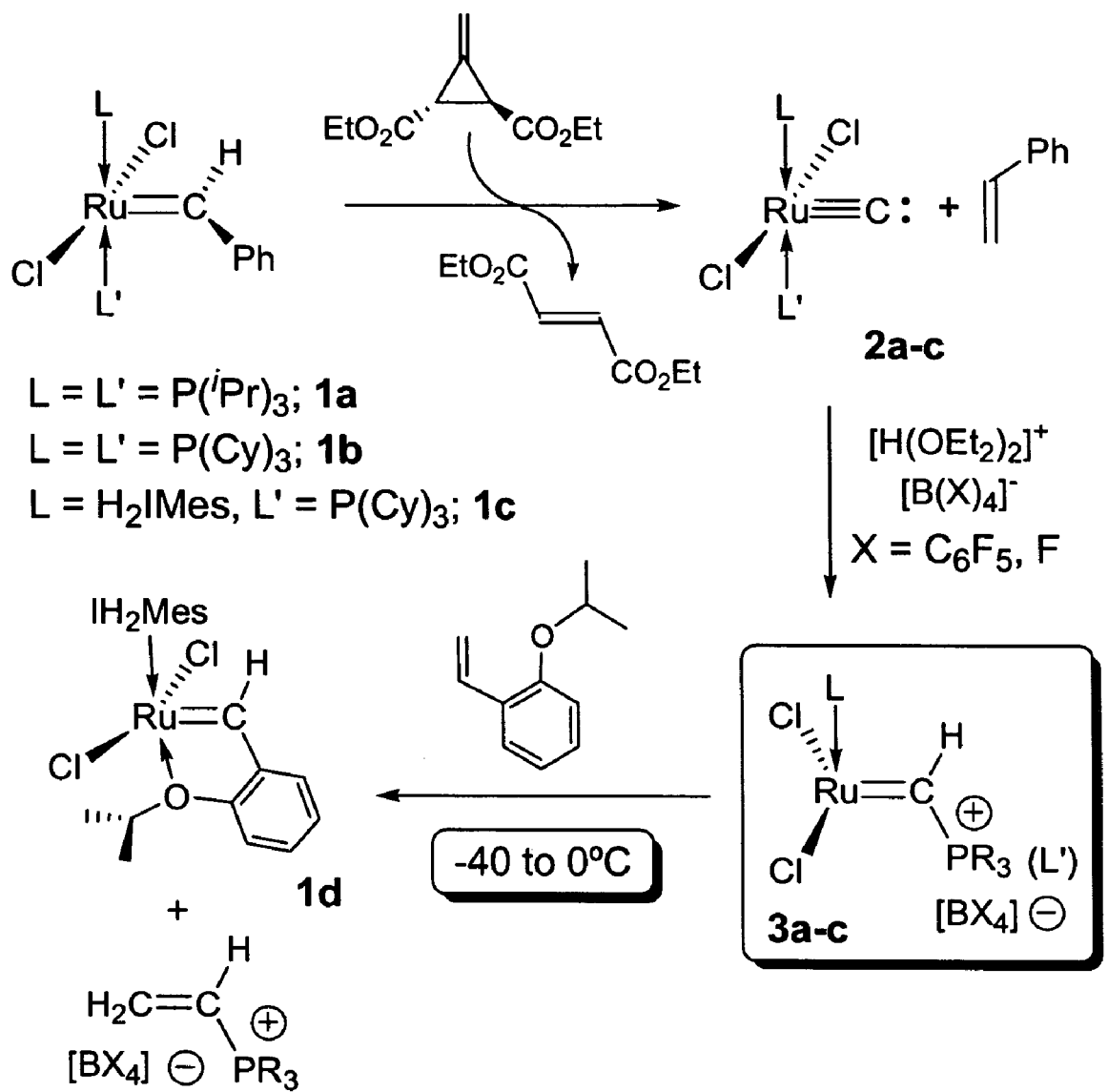
FIG. 1 schematically illustrates a method for synthesizing catalysts of the invention having the structure of formula (II), as described in Examples 1 through 7.

DETAILED DESCRIPTION OF THE INVENTION (I) Definitions and Nomenclature:

It is to be understood that unless otherwise indicated this invention is not limited to specific reactants, reaction conditions, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a catalyst" or "a complex" encompasses a combination or mixture of different catalysts or complexes as will as a single catalyst or complex, reference to "a substituent" includes a single substituent as well as two or more substituents that may or may not be the same, and the like.

In this specification and in the claims that follow, reference will be made to a number of terms, which shall be defined to have the following meanings:

The phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl," as used herein and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, and fluoro or iodo substituent.

The term "fluorinated" is used in the conventional sense to refer to the replacement of a hydrogen atom in a molecule or molecular segment with a fluorine atom. The term "perfluorinated" is also used in the conventional sense to refer to a molecule or molecular segment wherein all hydrogen atoms are replaced with fluorine atoms. Thus, a "fluorinated" methyl group includes —CH$_2$F and —CHF$_2$ as well as the "perfluorinated" methyl group trifluoromethyl, i.e., —CF$_3$.

"Hydrocarbyl" refers to univalent hydrocarbyl radicals containing 1 to about 30 carbon atoms, preferably 1 to about 20 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_6$-$C_{20}$ aralkyloxy, $C_6$-$C_{20}$ alkaryloxy, acyl (including $C_2$-$C_{20}$ alkylcarbonyl (—CO-alkyl) and $C_6$-$C_{20}$ arylcarbonyl (—CO-aryl)), acyloxy (—O-acyl, including $C_2$-$C_{20}$ alkylcarbonyloxy (—O—CO-alkyl) and $C_6$-$C_{20}$ arylcarbonyloxy (—O—CO-aryl)), $C_2$-$C_{20}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{20}$ alkyl)-substituted carbamoyl (—(CO)—NH($C_1$-$C_{20}$ alkyl)), di-($C_1$-$C_{20}$ alkyl)-substituted carbamoyl (—(CO)—N($C_1$-$C_{20}$ alkyl)$_2$), mono-($C_5$-$C_{20}$ aryl)-substituted carbamoyl (—(CO)—NH-aryl), di-($C_5$-$C_{20}$ aryl)-substituted carbamoyl (—(CO)—N($C_5$-$C_{20}$ aryl)$_2$), di-N—($C_1$-$C_{20}$ alkyl),N—($C_5$-$C_{20}$ aryl)-substituted carbamoyl, thiocarbamoyl (—(CS)—NH$_2$), mono-($C_1$-$C_{20}$ alkyl)-substituted thiocarbarnoyl (—(CO)—NH($C_1$-$C_{20}$ alkyl)), di-($C_1$-$C_{20}$ alkyl)-substituted thiocarbamoyl (—(CO)—N($C_1$-$C_{20}$ alkyl)$_2$), mono-($C_5$-$C_{20}$ aryl)-substituted thiocarbamoyl (—(CO)—NH-aryl), di-($C_5$-$C_{20}$ aryl)-substituted thiocarbamoyl (—(CO)—N($C_5$-$C_{20}$ aryl)2), di-N—($C_1$-$C_{20}$ alkyl),N—($C_5$-$C_{20}$ aryl)-substituted thiocarbanoyl, carbamido (—NH—(CO)—$NH_2$), cyano(—C≡N), cyanato (—O—C≡N), thiocyanato (—S—C≡N), isocyano (—N+≡$C^-$), formyl (—(CO)—H), thioformyl (—(CS)—H), amino (—$NH_2$), mono-($C_1$-$C_{20}$ alkyl)-substituted amino, di-($C_1$-$C_{20}$ alkyl)-substituted amino, mono-($C_5$-$C_{20}$ aryl)-substituted amino, di-($C_5$-$C_{20}$ aryl)-substituted amino, $C_2$-$C_{20}$ alkylamido (—NH—(CO)-alkyl), $C_6$-$C_{20}$ arylamido (—NH—(CO)-aryl), imino (—CR=NH where R=hydrogen, $C_1$-$C_{20}$ alkyl, $C_5$-$C_{20}$ aryl, $C_6$-$C_{20}$ alkaryl, $C_6$-$C_{20}$ aralkyl, etc.), $C_2$-$C_{20}$ alkylimino (—CR=N(alkyl), where R=hydrogen, $C_1$-$C_{20}$ alkyl, $C_5$-$C_{20}$ aryl, $C_6$-$C_{20}$ alkaryl, $C_6$-$C_{20}$ aralkyl, etc.), arylimino (—CR=N(aryl), where R=hydrogen, $C_1$-$C_{20}$ alkyl, $C_5$-$C_{20}$ aryl, $C_6$-$C_{20}$ alkaryl, $C_6$-$C_{20}$ aralkyl, etc.), nitro (—$NO_2$), nitroso (—NO), sulfo (—$SO_2$—OH), sulfonato (—$SO_2$—$O^-$), $C_1$-$C_{20}$ alkylsulfanyl (—S-alkyl; also termed "alkylthio"), $C_5$-$C_{20}$ arylsulfanyl (—S-aryl; also termed "arylthio"), $C_1$-$C_{20}$ alkyldithio (—S—S-alkyl), $C_5$-$C_{20}$ aryldithio (—S—S-aryl), $C_1$-$C_{20}$ alkylsulfinyl (—(SO)-alkyl), $C_5$-$C_{20}$ arylsulfinyl (—(SO)-aryl), $C_1$-$C_{20}$ alkylsulfonyl (—$SO_2$-alkyl), $C_5$-$C_{20}$ arylsulfonyl (—$SO_2$-aryl), boryl (—$BH_2$), borono (—$B(OH)_2$), boronato (—$B(OR)_2$ where R is alkyl or other hydrocarbyl), phosphono (—$P(O)(OH)_2$), phosphonato (—$P(O)(O^-)_2$), phosphinato (—$P(O)(O^-)$), phospho (—$PO_2$), phosphino (—$PH_2$), silyl (—$SiR_3$ wherein R is hydrogen or hydrocarbyl), and silyloxy (—O-silyl); and the hydrocarbyl moieties $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{20}$ alkynyl (preferably $C_2$-$C_{12}$ alkynyl, more preferably $C_2$-$C_6$ alkynyl), $C_5$-$C_{20}$ aryl (preferably $C_5$-$C_{14}$ aryl), $C_6$-$C_{20}$ alkaryl (preferably $C_6$-$C_{16}$ alkaryl), and $C_6$-$C_{20}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The term "olefin metathesis" is used in the now-conventional sense to refer to the metal-catalyzed redistribution of carbon-carbon bonds in a reaction involving an olefin.

When a modifier term appears prior to a list of two or more elements, it is intended that the term apply to every element of the list. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn.

(II) The Organometallic Complexes:

The organometallic complexes of the invention have the structure of formula (I)

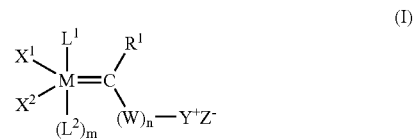

wherein M, $L^1$, $L^2$, $X^1$, $X^2$, $R^1$, W, Y, Z, m and n are as follows.

M, which serves as the transition metal center, is a Group 8 transition metal, particularly ruthenium or osmium. In a particularly preferred embodiment, M is ruthenium.

$X^1$ and $X^2$ are anionic ligands, and may be the same or different, or may be linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxy-carbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{20}$ aryl, and halide, which may, in turn, with the exception of halide, be further substituted with one or more groups selected from halide, $C_1$-$C_6$ alkyl, $C_1$-$C_6$ alkoxy, and phenyl. In the latter case, i.e., when $X^1$and $X^2$ are substituted, fluoride substituents are preferred, giving rise to fluorinated and perfluorinated anionic ligands. In more preferred embodiments, $X^1$ and $X^2$ are selected from halide, mesylate, tosylate, fluorinated $C_2$-$C_{20}$ acyloxy (e.g., trifluoroacetate, $CF_3CO_2$), fluorinated $C_1$-$C_{20}$ alkylsulfonate (e.g., trifluoromethanesulfonate, $CF_3SO_3$; also referred to as "triflate"), fluorinated $C_1$-$C_{20}$ alkoxy (e.g., hexafluoroisopropoxide, $(CF_3)_2CHO$), and fluorinated $C_5$-$C_{20}$ aryloxy (e.g., perfluorophenoxy, $C_6F_5O$). In the most preferred embodiment, $X^1$ and $X^2$ are each chloride.

$R^1$ is selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{20}$ aryl, $C_6$-$C_{20}$ alkaryl, $C_6$-$C_{20}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{20}$ aryl, $C_6$-$C_{20}$ alkaryl, $C_6$-$C_{20}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{20}$ alkaryl, $C_6$-$C_{20}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{20}$ aryl, $C_6$-$C_{20}$ alkaryl, $C_6$-$C_{20}$ aralkyl, etc.), and functional groups. Typically, $R^1$ is hydrogen, $C_1$-$C_{12}$ hydrocarbyl, or substituted $C_1$-$C_{12}$ hydrocarbyl, preferably hydrogen or $C_1$-$C_{12}$ alkyl, and optimally hydrogen.

$L^1$ and $L^2$ are neutral electron donor ligands, and m is zero or 1, meaning that $L^2$ is optional. Examples of suitable $L^1$ moieties include, without limitation, phosphine, sulfonated phosphine, phosphite, phosphinite, phosphonite, arsine, stilbine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), thioether, and heteroatom-substituted carbene, and examples of suitable $L^2$ moieties include, without limitation, phosphine, sulfonated phosphine, phosphite, phosphinite, phosphonite, arsine, stilbine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. Preferred $L^1$ ligands are N-heterocyclic carbenes and phosphines, and preferred $L^2$ ligands are phosphines. Exemplary phosphines are of the formula $PR^5R^6R^7$, where $R^5$, $R^6$, and $R^7$ are each independently aryl or $C_1$-$C_{10}$ alkyl, particularly primary alkyl, secondary alkyl, or cycloalkyl. Such phosphines include, for example, tricyclohexylphosphine, tricyclopentylphosphine, triisopropylphosphine, triphenylphosphine, diphenylmethylphosphine, or phenyldimethylphosphine, with tricyclohexylphosphine and tricyclopentylphosphine. It is also to be understood that when complexes of the invention represented as containing a single neutral electron donor ligand ($L^1$, and not $L^2$) are in a polar organic solvent or in a reaction mixture, the transition metal center may associate with the polar solvent molecules (e.g., water, ketones, aldehydes, organohalides, or the like) or with a substrate (e.g., acrylonitrile).

W is an optionally substituted and/or heteroatom-containing $C_1$-$C_{20}$ hydrocarbylene linkage, typically an optionally substituted $C_1$-$C_{12}$ alkylene linkage, e.g., —$(CH_2)_i$— where i is an integer in the range of 1 to 12 inclusive and any of the hydrogen atoms may be replaced with a non-hydrogen substituent as described earlier herein with regard to the definition of the term "substituted." The subscript n is zero or 1, meaning that W may or may not be present. In a preferred embodiment, n is zero.

Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Preferably, Y is a $C_1$-$C_{12}$ hydrocarbyl-substituted, positively charged Group 15 or Group 16 element. Representative Y groups include $P(R^2)_3$, $P(R^2)_3$, $As(R^2)_3$, $S(R^2)_2$, $O(R^2)_2$, where the $R^2$ are independently selected from $C_1$-$C_{12}$ hydrocarbyl; within these, preferred Y groups are phosphines of the structure $P(R^2)_3$ wherein the $R^2$ are independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y can also be a heterocyclic group containing the positively charged Group 15 or Group 16 element. For instance, when the Group 15 or Group 16 element is nitrogen, Y may be an optionally substituted pyridinyl, pyrazinyl, or imidazolyl group.

$Z^-$ is a negatively charged counterion associated with the cationic complex, and may be virtually any anion, so long as the anion is inert with respect to the components of the complex and the reactants and reagents used in the metathesis reaction catalyzed. Preferred $Z^-$ moieties are weakly coordinating anions, such as, for instance, $[B(C_6F_5)_4]^-$, $[BF_4]^-$, $[B(C_6H_6)_4]^-$, $[CF_3S(O)_3]^-$, $[PF_6]^-$, $[SbF_6]^-$, $[AlCl_4]^-$, $[FSO_3]^-$, $[CB_{11}H_6Cl_6]^-$, $[CB_{11}H_6Br_6]^-$, and $[SO_3F:SbF_5]^-$. Preferred anions suitable as $Z^-$ are of the formula $B(R^{15})_4^-$ where $R^{15}$ is fluoro, aryl, or perfluorinated aryl, typically fluoro or perfluorinated aryl. Most preferred anions suitable as $Z^-$ are $BF_4^-$ and $B(C_6F_5)^-$, optimally the latter.

It should be emphasized that any two or more of $X^1$, $X^2$, $L^1$, $L^2$, $R^1$, W, and Y can be taken together to form a cyclic group, as disclosed, for example, in U.S. Pat. No. 5,312,940 to Grubbs et al. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (I) of this section.

One group of exemplary catalysts encompassed by the structure of formula (I) are those wherein m and n are zero, such that the complex has the structure of formula (II)

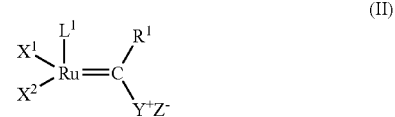

(II)

Possible and preferred $X^1$, $X^2$, and $L^1$ ligands are as described earlier with respect to complexes of formula (I), as are possible and preferred $Y^+$ and $Z^-$ moieties. M is Ru or Os, preferably Ru, and $R^1$ is hydrogen or $C_1$-$C_{12}$ alkyl, preferably hydrogen.

In formula (II)-type catalysts, $L^1$ is preferably a heteroatom-containing carbene ligand having the structure of formula (III)

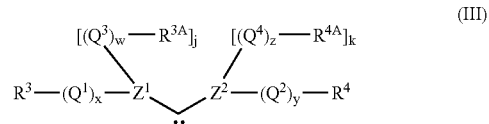

(III)

such that the complex (II) is then has the structure of formula (IV)

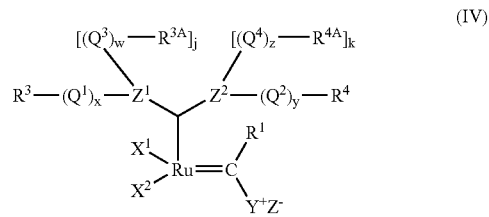

(IV)

wherein $X^1$, $X^2$, $R^1$, $R^2$, Y, and Z are as defined previously, and the remaining substituents are as follows:

$Z^1$ and $Z^2$ are heteroatoms typically selected from N, O, S, and P. Since O and S are divalent, j is necessarily zero when $Z^1$ is O or S, and k is necessarily zero when $Z^2$ is O or S. However, when $Z^1$ is N or P, then j is 1, and when $Z^2$ is N or P, then k is 1. In a preferred embodiment, both $Z^1$ and $Z^2$ are N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z are independently zero or 1, meaning that each linker is optional. Preferably, w, x, y, and z are all zero.

$R^3$, $R^{3A}$, $R^4$, and $R^{4A}$ are independently selected from hydrogen, hydrogen, $C_1$-$C_{20}$ hydrocarbyl, substituted $C_1$-$C_{20}$ hydrocarbyl, heteroatom-containing $C_1$-$C_{20}$ hydrocarbyl, and substituted heteroatom-containing $C_1$-$C_{20}$ hydrocarbyl.

Preferably, w, x, y, and z are zero, $Z^1$ and $Z^1$ are N, and $R^{3A}$ and $R^{4A}$ are linked to form —Q—, such that the complex has the structure of formula (V)

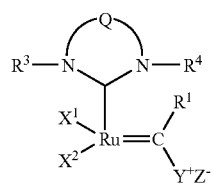

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q is often, although not necessarily, a two-atom linkage or a three-atom linkage, e.g., —CH$_2$—CH$_2$—, —CH(Ph)-CH(Ph)- where Ph is phenyl; =CR—N=, giving rise to an unsubstituted (when R=H) or substituted (R=other than H) triazolyl group; or —CH$_2$—SiR$_2$—CH$_2$— (where R is H, alkyl, alkoxy, etc.).

In a more preferred embodiment, Q is a two-atom linkage having the structure —CR$^8$R$^9$—CR$^{10}$R$^{11}$— or —CR$^8$=CR$^{10}$—, preferably —CR$^8$R$^9$—CR$^{10}$R$^{11}$—, wherein $R^8$, $R^9$, $R^{10}$, and $R^{11}$ are independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups as defined in part (I) of this section. Examples of functional groups here include carboxyl, $C_1$-$C_{20}$ alkoxy, $C_5$-$C_{20}$ aryloxy, $C_2$-$C_{20}$ alkoxycarbonyl, $C_2$-$C_{20}$ alkoxycarbonyl, $C_2$-$C_{20}$ acyloxy, $C_1$-$C_{20}$ alkylthio, $C_5$-$C_{20}$ arylthio, $C_1$-$C_{20}$ alkylsulfonyl, and $C_1$-$C_{20}$ alkylsulfinyl, optionally substituted with one or more moieties selected from $C_1$-$C_{10}$ alkyl, $C_1$-$C_{10}$ alkoxy, $C_5$-$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and have the structure (VI)

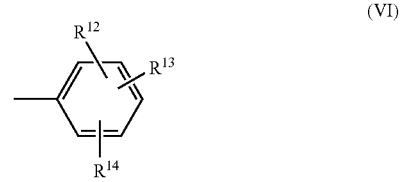

in which $R^{12}$, $R^{13}$, and $R^{14}$ are each independently hydrogen, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{20}$ aryl, substituted $C_5$-$C_{20}$ aryl, $C_5$-$C_{20}$ heteroaryl, $C_5$-$C_{30}$ aralkyl, $C_5$-$C_{30}$ alkaryl, or halide. Preferably, $R^{12}$, $R^{13}$, and $R^{14}$ are each independently hydrogen, $C_1$-$C_{10}$ alkyl, $C_1$-$C_{10}$ alkoxy, $C_5$-$C_{14}$ aryl, substituted $C_5$-$C_{14}$ aryl, or halide. More preferably, $R^3$ and $R^4$ are mesityl (2,4,6-trimethylphenyl).

Exemplary organometallic complexes having the general structure (II) are those wherein:

$L^1$ is 1,3-dimesitylimidazole-2-ylidene (IMes) or 1,3-dimesityl-4,5-dihydroimidazol-2-ylidene (H$_2$IMes);

$X^1$ and $X^2$ are chloro;

Y is P(R$^2$)$_3$, wherein the R$^2$ are independently selected from $C_1$-$C_6$ alkyl and phenyl; and $Z^-$ is BF$_4^-$ or B(C$_6$F$_5$)$_4^-$.

It will be appreciated that organometallic complexes having the structure of formula (I) wherein m is zero (such that no $L^2$ is present), including but not limited to complexes of formula (II), are highly active olefin metathesis catalysts. Without wishing to be bound by theory, it is presumed that the high activity is due to the absence of a second electron-donating ligand. That is, it has been shown experimentally (Dias et al. (1997) *J. Am. Chem. Soc.* 119:3887 and Adhart et al. (2000) *J. Am. Chem. Soc.* 122:8204) and computationally (Adhart et al. (2004) *J. Am. Chem. Soc.* 126:3496 and Cavallo (2002) *J. Am. Chem. Soc.* 124:8965) that in the known catalysts (PCy$_3$)$_2$(Cl)$_2$Ru=CHPh (D) and (IMesH$_2$)(PCy$_3$)(Cl)$_2$Ru=CHPh (E)

D:

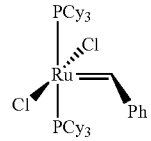

E:

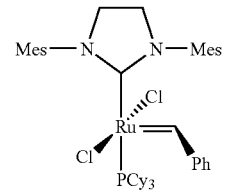

(wherein "Cy" represents cyclohexyl, "Mes" represents mesitylene, and "Ph" represents phenyl), the reactive species is the 14-electron alkylidene complex Cl$_2$(L)Ru=C(H)Ph, wherein L is tricyclohexylphosphine or H$_2$IMes, respectively. This reactive species is formed upon dissociation of the second electron donor ligand (tricyclohexylphosphine, in the aforementioned examples), a process that is reversible. It will thus be appreciated that with catalysts such as those of formula (II), the absence of a second electron donor ligand improves the kinetics of initiation by circumventing the initiation step completely.

Another group of catalysts encompassed by the structure of formula (I) are those wherein M is Ru or Os, preferably Ru, $R^1$ is hydrogen or $C_1$-$C_{12}$ alkyl, preferably hydrogen, and both m and n are 1, such that the complex has the structure of formula (VII)

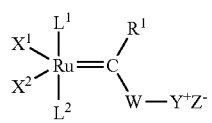
(VII)

As with complexes of formula (II), possible and preferred $X^1$, $X^2$, $L^1$, and $L^2$ ligands in complexes of formula (VII) are as described earlier with respect to complexes of formula (I), as are possible and preferred W, $Y^+$, and $Z^-$ moieties.

Exemplary organometallic complexes having the general structure (VII) are those wherein:

$L^1$ is 1,3-dimesitylimidazole-2-ylidene (IMes) or 1,3-dimesityl-4,5-dihydroimidazol-2-ylidene ($H_2$IMes);

$L^2$ is selected from tricyclohexylphosphine, tricyclopentylphosphine, triisopropylphosphine, triphenylphosphine, diphenylmethylphosphine, and phenyldimethylphosphine;

W is an optionally substituted $C_1$-$C_{12}$ alkylene linkage;

$X^1$ and $X^2$ are chloro;

Y is $P(R^2)_3$, wherein the $R^2$ are independently selected from $C_1$-$C_6$ alkyl and phenyl; and $Z^-$ is $BF_4^-$ or $B(C_6F_5)^-$.

Representative organometallic complexes of the invention thus include, without limitation, the following specific structures 1 through 12:

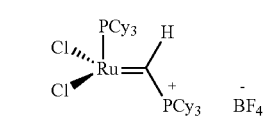
1

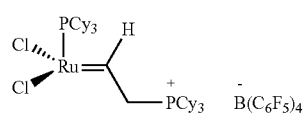
2

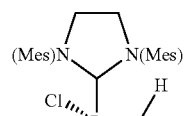
3

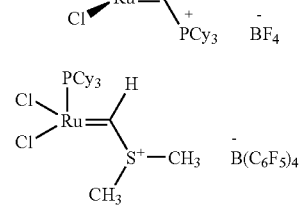
4

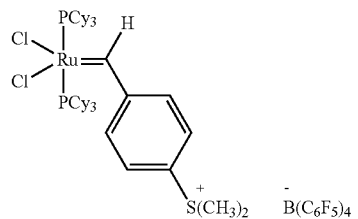
5

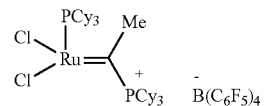
6

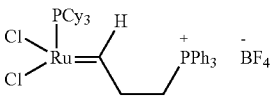
7

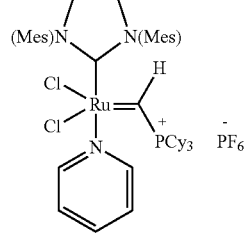
8

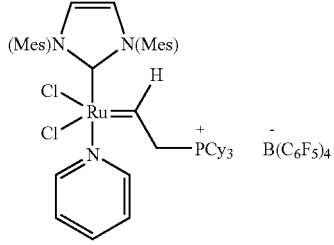
9

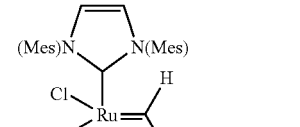
10

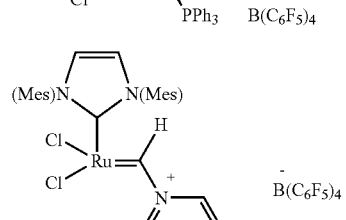
11

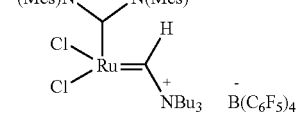
12

The organometallic complexes of the invention have been shown to be stable to oxygen and ambient moisture as well as thermally stable. It additionally appears that these catalysts may be stable indefinitely in the solid state when stored at room temperature. Metathesis reactions with functionalized olefins also proceed efficiently, providing the desired product at a high yield with relative small quantities of the catalytic complex.

(III) Synthesis of the Complexes:

The organometallic complexes of the invention are synthesized from Group 8 transition metal carbenes having the structure of formula (XVI)

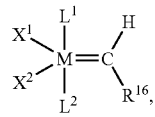

(XVI)

or from Group 8 transition metal carbides prepared therefrom, wherein M, $L^1$, $L^2$, $X^1$, and $X^2$ are as defined previously, and $R^{16}$ is $C_1$-$C_{20}$ hydrocarbyl.

For example, an organometallic complex having the structure of formula (XI)

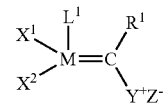

(XI)

wherein M is a Group 8 transition metal, $L^1$ is a neutral electron donor ligand, $X^1$ and $X^2$ are anionic ligands, $R^1$ is hydrogen, $C_1$-$C_{12}$ hydrocarbyl, or substituted $C_1$-$C_{12}$ hydrocarbyl, Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, and $Z^-$ is a negatively charged ion, may be synthesized by contacting a Group 8 transition metal carbide having the structure (XIII)

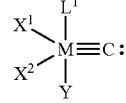

(XIII)

with an ionic reagent of the formula $[R^1]^+[Z]^-$. The $[R^1]^+$ moiety in the ionic reagent is typically hydrogen, and may be associated with a polar solvent (as in $[H(Et_2O)_2][B(C_6F_5)_4]^-$; see Jutzi et al. (2000), cited supra). Preferred $Z^-$ moieties, as noted earlier herein, are weakly coordinating anions, such as, for instance, $[B(C_6F_5)_4]^-$, $[BF_4]^-$, $[B(C_6H_6)_4]^-$, $[CF_3S(O)_3]^-$, $[PF_6]^-$, $[SbF_6]^-$, $[AlCl_4]^-$, $[FSO_3]^-$, $[CB_{11}H_6Cl_6]^-$, $[CB_{11}H_6Br_6]^-$, and $[SO_3F{:}SbF_5]^-$, with $[B(C_6F_5)_4]^-$ and $[BF_4]^-$ particularly preferred. Suitable ionic reagents thus include, without limitation, $[H(Et_2O)_2][B(C_6F_5)_4]$, $[H(Et_2O)_2][BF_4]$, $BF_3/HF$, $HB(C_6H_6)_4$, $CF_3S(O)_3H$, $HF—PF_5$, $HF—SbF_5$, $CHCCl_3{:}AlCl_3$, $HSO_3F{:}SbF_5$, and $FSO_3H$.

The invention also provides a method for synthesizing an organometallic complex having the structure of formula (II)

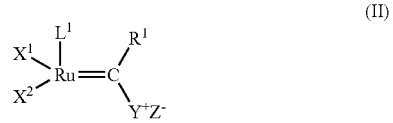

(II)

wherein $L^1$, $X^1$, $X^2$, $R^1$, and Y are as defined previously, with Y preferably being a $C_1$-$C_{12}$ hydrocarbyl-substituted, positively charged Group 15 or Group 16 element, and $Z^-$ is of the formula $B(R^{15})_4^-$ where $R^{15}$ is fluoro, aryl, or perfluorinated aryl, the method comprising:

(a) contacting (i) a ruthenium complex having the structure (XIV)

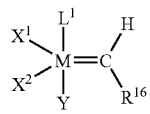

(XIV)

where $R^{16}$ is $C_1$-$C_{20}$ hydrocarbyl, with (ii) a reagent effective to convert the ruthenium complex to the ruthenium carbide (XV)

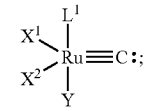

(XV)

and (b) contacting the ruthenium carbide with a protonating reagent of the formula $[H(OR_2)_2]^+[B(R^{15})_4]^-$ where R is $C_1$-$C_6$ hydrocarbyl.

The following scheme illustrates this synthesis:

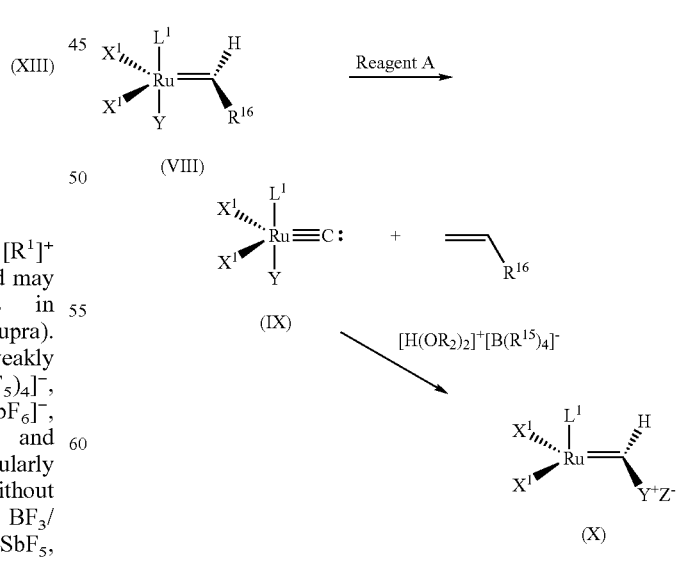

In the initial step of the reaction, the ruthenium complex (VIII) $((X^1X^2)(L^1Y)Ru{=}CHR^{16})$ is contacted with a reagent (identified as "Reagent A" in the scheme) effective to convert the ruthenium complex to the ruthenium carbide (IX) ((X$^1$X$^2$)(Y)Ru≡C:). As indicated in the examples, an exemplary reagent for this purpose is the methylene cyclopropane olefin known as Feist's ester, having the structure

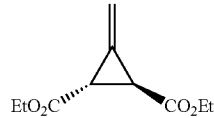

The reaction between complex (VIII) and Feist's ester is a metathesis reaction that results in elimination of diethyl flumarate (EtO$_2$C—CH═CH—CO$_2$Et) and generation of the carbide (IX). Subsequent reaction involves protonation of the carbide (IX) with the electrophilic reagent [H(OR$_2$)$_2$]$^+$[B(R$^{15}$)$_4$]$^-$ and transfer of the ligand Y to the protonated carbide carbon atom, resulting in complex (X). See FIG. 1.

In a further embodiment, a method is provided for synthesizing an organometallic complex having the structure of formula (XII)

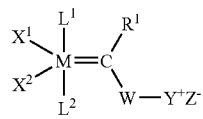

wherein M, L$^1$, X$^1$, X$^2$, R$^1$, and Y are as defined previously, W is an optionally substituted and/or heteroatom-containing C$_1$-C$_{20}$ hydrocarbylene linkage, Y is a positively charged Group 15 or Group 16 element substituted with hydrogen, C$_1$-C$_{12}$ hydrocarbyl, substituted C$_1$-C$_{12}$ hydrocarbyl, heteroatom-containing C$_1$-C$_{12}$ hydrocarbyl, or substituted heteroatom-containing hydrocarbyl, and Z$^-$ is a negatively charged ion, the method comprising contacting an organometallic complex having the structure (XVI)

Figure 2:
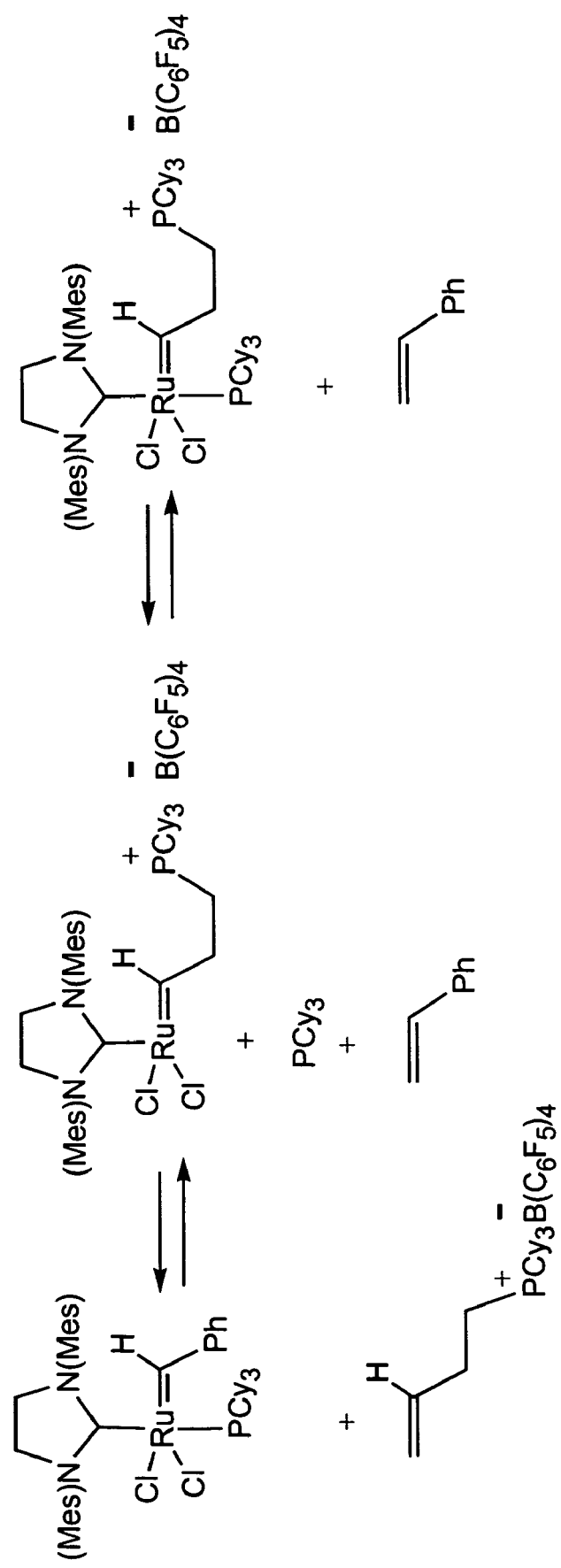
FIG. 2 schematically illustrates a method for synthesizing catalysts of the invention having the structure of formula (VII).

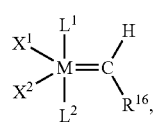

where R$^{16}$ is C$_1$-C$_{20}$ hydrocarbyl, with an ionic reagent having the structure H$_2$C═CR$^1$—W—Y$^+$Z$^-$ under conditions effective to enable cross metathesis between the transition metal alkylidene group in the complex and the olefinic moiety in the reagent. As illustrated in the reaction of Scheme 2, in FIG. 2, the complex (XVI) is in equilibrium with a complex lacking the L$^2$ moiety. Therefore, the aforementioned synthesis is also useful for preparing complexes of formula (I) wherein m is zero and n is 1.

In a further embodiment, the invention provides a method for synthesizing an organometallic complex of the invention having the structure of formula (VII)

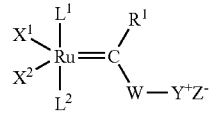

wherein L$^1$, L$^2$, X$^1$, X$^2$, R$^1$, W, Y are as defined previously, with Y preferably being a C$_1$-C$_{12}$ hydrocarbyl-substituted, positively charged Group 15 or Group 16 element, and Z$^-$ is of the formula B(R$^{15}$)$_4$$^-$ where R$^{15}$ is fluoro, aryl, or perfluorinated aryl, the method comprising contacting a ruthenium complex having the structure (XVII)

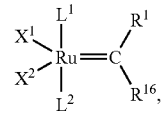

where R$^{16}$ is as defined above, with an ionic reagent having the structure H$_2$C═CR$^1$—W—Y$^+$Z$^-$, under conditions effective to enable cross metathesis between the ruthenium alkylidene group in the complex and the olefinic moiety in the reagent. This reaction is illustrated by the scheme set forth in FIG. 2.

(IV) Utility:

The organometallic complexes of the invention are useful in the catalysis of olefin metathesis reactions, including ROMP, RCM, ADMET, and XMET reactions. Accordingly, the invention provides, in a further embodiment, a method for catalyzing an olefin metathesis reaction, the method comprising contacting an olefinic reactant with a catalytically effective amount of an organometallic complex of the invention under reaction conditions effective to enable olefin metathesis. ROMP is carried out, by definition, with a cyclic olefin substrate, RCM and ADMET with acyclic dienes, and XMET with two olefinic reactants.

The reaction conditions are those normally used in olefin metathesis reactions catalyzed by the Grubbs family of metathesis catalysts, e.g., as described in U.S. Pat. Nos. 5,312,940, 5,342,909, 5,831,108, 5,969,170, 6,111,121, and 6,211,391 to Grubbs et al. The complexes may be dissolved in the reaction medium or attached to a solid support; as understood in the field of catalysis, suitable solid supports may be of synthetic, semi-synthetic, or naturally occurring materials, which may be organic or inorganic, e.g., polymeric, ceramic, or metallic. Attachment to the support may through ionic interaction or via a covalent linkage, and the covalent linkage may be direct or indirect; if indirect, the linkage will typically be between a functional group on a support surface and a ligand or substituent on the catalytic complex.

The complexes are also useful in the synthesis of "Grubbs-Hoveyda" catalysts in which a single moiety is covalently bound to the carbene carbon atom and contains a functionality that coordinates to the transition metal center. See Kingsbury et al. (1999) *J. Am. Chem. Soc.* 121:791; Hoveyda (1999) *J. Am. Chem. Soc.* 121:791; and Garber et al. (2000) *J. Am. Chem. Soc.* 122:8168. Such a reaction is illustrated in the following scheme:

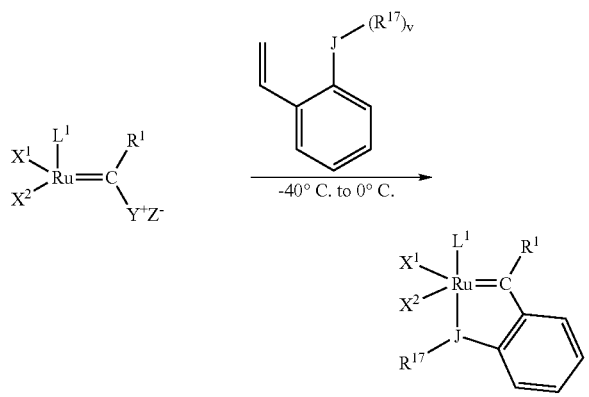

In the above scheme, $L^1$, $X^1$, $X^2$, $R^1$, Y, and $Z^-$ are as defined earlier herein; $R^1$ is usually hydrogen; J is a heteroatom that is capable of coordinating to Ru, e.g., O, S, N, etc., preferably O; $R^{17}$ is $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, preferably $C_1$-$C_6$ alkyl; and v is 1 or 2, representing the number of $R^{17}$ substituents bound to J.

A specific example of such a reaction is the following:

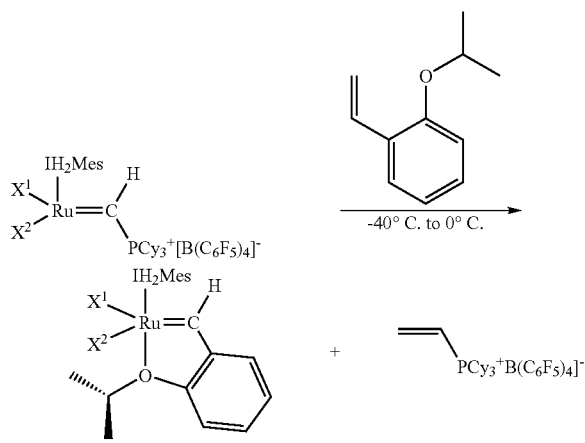

See Romero et al. (2004) *Angew. Chem. Int. Ed.* 43:6161-6165.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

Experimental:

The equipment and general procedures used in the Examples herein, as well as sources or syntheses of all reagents and starting materials, were as follows:

Argon-filled Innovative Technology System One dryboxes were used to store air and moisture sensitive compounds, and for manipulation of air sensitive materials. Reactions were performed either on a double manifold vacuum line using standard Schlenk techniques or under an argon atmosphere in the drybox for small-scale reactions. Diethyldiallylmalonate was purchased from Aldrich and used without further purification. $CH_2Cl_2$ was predried and stored in glass bombs over $CaH_2$ and distilled immediately prior to use. Pentane was stored and dried over a sodium mirror using benzophenone ketyl as indicator and vacuum distilled prior to use. $CD_2Cl_2$ was purchased from Cambridge Isotopes, dried over $CaH_2$, and stored in appropriate glass bombs after vacuum distillation.

Nuclear magnetic resonance (NMR) spectra were obtained on Bruker ACE-200 ($^1$H, 200.134 MHz), AMX 300 ($^1$H 300.138, $^{19}$F 282.371 MHz) and BAM-400 ($^1$H 400.134 MHz, $^{13}$C 100.614 MHz, $^{11}$B 128.377 MHz). All $^1$H and $^{13}$C spectra were referenced externally to $Me_4Si$ at 0 ppm by referencing the residual solvent peak. $^{11}$B NMR spectra were referenced to $BF_3 \cdot Et_2O$ at 0 ppm, while $^{19}$F spectra were referenced externally to $C_6F_6$ at −163 ppm relative to $CFCl_3$ at 0 ppm. Elemental analyses were performed using a Control Equipment Corporation 440 Elemental Analyzer.

$(i-Pr_3P)_2Cl_2Ru=CHPh$ (1a) and $(Cy_3P)_2Cl_2Ru=CHPh$ (1b) were prepared according to published procedures. $(H_2IMes)(Cy_3P)Cl_2Ru=CHPh$ (1c) was obtained from Materia, Inc. (Pasadena, Calif.). The Schrock Catalyst was purchased from Strem. Feist's acid was prepared according to the procedure described by Gilchrist and Rees (Gilchrist et al. (1968) *J. Chem. Soc.* (C), p. 769), starting from the commercially available ethyl isodehydracetate (97%, Acros Organics), following the described bromination to obtain ethyl 5-bromo-2,4-dimethyl-6-oxopyran-3-carboxylate. This a-pyrone was saponified following the reported procedure to obtain multigram quantities of Feist's acid. Fischer esterification of the diacid was accomplished by dissolving pale yellow Feist's acid in methanol and adding 2-3 drops of concentrated sulfuric acid. Upon stirring overnight the solution was worked up by removing the solvent in a rotavaporator leaving a pale yellow oil. The oil was redissolved in diethyl ether and treated twice with a 5% wt. solution of $NaHCO_3$, twice with distilled water, and dried over $MgSO_4$. Upon filtration and evaporation of the solvent a pale yellow oil was obtained, corresponding to pure Feist's dimethyl ester as judged by $^1$H NMR spectroscopy. The yield was quantitative. Additionally, solidification of the oil can be induced by cooling at −78° C. under vacuum. Upon thaw at room temperature the oil becomes a more manageable solid. The dimethyl ester was stored in a freezer due to its low melting point.

Example 1 through 7 describe the synthesis and characterization of the complexes prepared in Scheme 1, in FIG. 1.

EXAMPLE 1

Preparation of $(i-Pr_3P)_2Cl_2Ru=C$: (2a)

In the glovebox, a 50 mL round bottom flask equipped with a stir bar was charged with $(i-Pr_3P)_2Cl_2Ru=CHPh$ (1a, 1.00 g, 1.71 mmol), which was dissolved in ca. 15 ml of dry $CH_2Cl_2$. To this solution, 0.291 g (1.71 mmol) of Feist's ester dissolved in ca. 5 ml of $CH_2Cl_2$ were added at once via pipette with stirring. Within 1 minute, the color of the solution changes from purple to brown; stirring was continued for additional 20 minutes. The flask was then connected to a vacuum line and the solvent removed to dryness. Drying was continued for ca. 30 additional minutes to remove most of the styrene by-product. The flask was then opened to air and the solid residue was transferred to a sublimation apparatus, where the majority of the flumarate by-product was removed at 50-60° C. under dynamic vacuum for 1.5 hours. At this point some traces of organic material might remain (Feist's ester, styrene or fumarate, all <5%) which can be eliminated by suspending the complex in wet pentane, stirring for 1 minute and decanting the supernatant. By repeating this process twice, a brown solid corresponding to analytically pure carbide was obtained. Yield: 825 mg (96%). $^1$H NMR (CD$_2$Cl$_2$, 25° C.): d 1.43 (dd, 36H, (CH$_3$)—CH—P, $^3J_{H\text{-}H}$=7.2 Hz, $^3J_{P\text{-}H}$=14.1 Hz), d 2.71-2.79 (second order multiplet, 6H, (CH$_3$)—CH—P). $^{31}$P{$^1$H} NMR (CD$_2$Cl$_2$, 25° C.)=d 46.9 (s, Ru—P$^i$Pr$_3$). $^{13}$C{$^1$H} NMR (CD$_2$Cl$_2$, 25° C.): d 19.81 (s, (CH$_3$)—CH—P), 22.94 (app. t, (CH$_3$)—CHP,"J$_{C\text{-}P}$"=13.8 Hz), d 472.9 (Ru≡C).

EXAMPLE 2

Preparation of (Cy$_3$P)$_2$Cl$_2$Ru≡C: (2b)

Using a procedure similar to the one outlined for 2a in Example 1, 2b was obtained in 90-95% yield. Spectral parameters matched those previously reported (i.e., by Carlson (2002) *J. Am. Chem. Soc.* 124:1580).

EXAMPLE 3

Preparation of (H$_2$IMes)(Cy$_3$P)Cl$_2$Ru≡C: (2c)

In the glovebox, a 50 ml round bottom flask equipped with a stir bar was charged with (H$_2$IMes)(Cy$_3$P) Cl$_2$Ru=CHPh (1c, 1.50 g, 1.76 mmol), which was dissolved in ca 20 ml of dry CH$_2$Cl$_2$. To this solution, 0.300 g (1.76 mmol) of Feist's ester dissolved in ca. 10 ml of CH$_2$Cl$_2$ were added at once via pipette with stirring. By contrast to the preparations of 2a-b, no immediate visible change was observed and the solution was stirred overnight (separate NMR experiments indicated that at this concentration, the reaction takes ca. 4 hrs. to reach completion). Work-up procedures were identical to those described above for 2a-b, resulting in a brown solid corresponding to pure carbide 2c was obtained. Yield: 1.22 g (90%).

EXAMPLE 4

Synthesis of [(i-Pr$_3$P)Cl$_2$Ru=CH(Pi-Pr$_3$)]$^+$[B(C$_6$F$_5$)$_4$]$^-$ (3a)

In the glovebox, (i-Pr$_3$P)$_2$Cl$_2$Ru≡C: (2a, 400 mg, 0.793 mmol) and [H(Et$_2$O)$_2$]$^+$[B(C$_6$F$_5$)$_4$]$^-$ (657 mg, 0.793 mmol) were weighed into a 50 ml round bottom flask. The flask was then fitted with a glass connector with a Kontes valve and attached to the vacuum line. The flask was evacuated and CH$_2$Cl$_2$ (20 ml) was condensed onto the solids at −78° C., using a dry ice/acetone cooling bath. The solution was then allowed to warm to room temperature and stirred for an additional hour. The solvent was then removed under vacuum leaving a solid residue. The system was then placed in the glovebox and the solid residue redissolved in ca 8 ml of CH$_2$Cl$_2$ and transferred to a glass vial. The solution was layered with pentane and allowed to diffuse at room temperature overnight, yielding burgundy crystals of [($^i$Pr$_3$P)Cl$_2$Ru=CH(P$^i$Pr$_3$)][B(C$_6$F$_5$)$_4$]. The yield is improved by cooling to −35° C. after diffusion has taken place. Yield: 895 mg, 95%. $^1$H NMR (CD$_2$Cl$_2$, 25° C.): d 1.38 (dd, 18H, Ru=CH—PCH(CH$_3$)$_2$, $^3J_{H\text{-}H}$=7.3 Hz, $^3J_{P\text{-}H}$=16.5 Hz), d 1.42 (dd, 18H, Ru—PCH(CH$_3$), $^3J_{H\text{-}H}$=7.1 Hz, $^3J_{P\text{-}H}$=15.7 Hz), d 2.69-2.63 (second order multiplet, 3H, (CH$_3$)—CH—P, $^3J_{H\text{-}H}$=7.1 Hz), d 3.00-2.93 (second order multiplet,3H, (CH$_3$)—CH—P, $^3J_{H\text{-}H}$=7.2 Hz), d 17.35 (dd, 1H, Ru=CH, $^2J_{P\text{-}H}$=36 Hz, $^3J_{P\text{-}H}$=1.8 Hz). $^{13}$P{$^1$H} NMR (CD$_2$Cl$_2$, 25° C.)=d 97.6 (s, 1P, Ru—P$^i$Pr$_3$), d 57.6 (s, 1P, Ru=CH—P$^i$Pr$_3$). $^{11}$B NMR=d-17.5 (s, B(C$_6$F$_5$)$_4$). $^{13}$C{$^1$H} NMR (CD$_2$Cl$_2$, 25° C.):d 17.7 (s, (CH3)—CH—P), d 19.5 (s, (CH$_3$)—CH—P), 22.0 (d, (CH$_3$)—CH—P, $^1J_{C\text{-}P}$=39.6 Hz), d 27.6 (d, (CH$_3$)—CH—P, $^1J_{C\text{-}P}$=26.7 Hz), d 136.3 (dt,$^1J_{C\text{-}F}$=244.5 Hz) 138.3 (dt $^1J_{C\text{-}F}$=244.8 Hz) and 148.2 (d, $^1J_{C\text{-}F}$=240.6 Hz) all B(C$_6$F$_5$)$_4$ signals, d 240.5 (broad, Ru=CH).

EXAMPLE 5

Synthesis of [(i-Pr$_3$P)Cl$_2$Ru=CH(PiPr$_3$)]$^+$(BF$_4$)$^-$

This example describes preparation of a complex analogous to that prepared in the preceding example, but as the BF$_4$$^-$ salt instead of the B(C$_6$F$_5$)$_4$$^-$ salt:

The compound (i-Pr$_3$P)$_2$Cl$_2$Ru≡C: (2a, 271 mg, 0.537 mmol) was weighed into a two-neck 50 ml round bottom flask equipped with a stir bar and a septum in the lateral neck, and the system was evacuated in the vacuum line. CH$_2$Cl$_2$ (20 ml) was condensed onto the solid and the system warmed up to room temperature. Then, a 54% wt. solution of HBF$_4$ in diethyl ether (74 mL, 0.537 mmol) was injected at room temperature and an immediate change to a darker brown-green color was observed. The solution was stirred for 1 hour at which time the solvent was removed under vacuum. The system was transferred to the glovebox and the solid residue obtained after evaporation was redissolved in the minimal amount of CH$_2$Cl$_2$ (ca. 2 ml). Addition of pentane results in the precipitation of a green microcrystalline solid. The solvent was decanted via pipette and the solid dried under high vacuum. Yield: 224 mg, 70%. $^1$H NMR (CD$_2$Cl$_2$, 25° C.): d 1.38 (dd,18H, (CH$_3$)—CH—P, $^3J_{P\text{-}H}$=6.8 Hz, $^3J_{H\text{-}H}$=5.5 Hz), d 1.42 (dd, 18H, (CH$_3$)—CH—P, $^3J_{P\text{-}H}$=7.0 Hz, $^3J_{H\text{-}H}$=4.3 Hz), d 2.69-2.80 (second order multiplet, 3H, (CH$_3$)—CH—P), d 3.17-3.06 (second order multiplet, 3H, (CH$_3$)—CH—P), d 17.65 (d, 1H, Ru=CH, $^2J_{P\text{-}H}$=35.5 Hz). $^{31}$P{$^1$H} NMR (CD$_2$Cl$_2$, 25° C.)=d 97.8 (s, 1P, Ru—P$^i$Pr$_3$), d 58.5 (s, 1P, Ru=CH—P$^i$Pr$_3$). $^{11}$B NMR=d-1.9 (s, BF$_4$).

EXAMPLE 6

Synthesis of [(Cy$_3$P)Cl$_2$Ru=CH(PCy$_3$)]$^+$[B(C$_6$F$_5$)$_4$]$^-$ (3b)

(Cy$_3$P)$_2$Cl$_2$Ru≡C: (2b, 150 mg, 0.201 mmol) and [H(Et$_2$O)$_2$]$^+$[B(C$_6$F$_5$)$_4$]$^-$ (166 mg, 0.201 mmol) were placed into a 25 ml round bottom flask, which was fitted with a glass connector with a Kontes valve and attached to the vacuum line. The flask was evacuated and CH$_2$Cl$_2$ (15 ml) was vacuum transferred onto the solids at −78° C. The system was warmed to room temperature and stirred for 1 hour. The solvent was then removed under vacuum leaving a brown residue. Pentane (20 ml) was vacuum transferred onto the residue and the system was sonicated for 5 minutes, leaving a green-purple residue. After allowing the solid to settle, the solvent was decanted via cannula, and the purple powder left was dried under full vacuum overnight. Yield: 250 mg, 87%. Alternatively, the product can be recrystallized by dissolving in $CH_2Cl_2$ (10 ml) and layering with pentane (10 ml). Upon diffusion of the two phases for 3-4 days, dark purple crystals are obtained in virtually quantitative yield. $^1H$ NMR ($CD_2Cl_2$, 25° C.): d 1.18-1.96 (complex set of multiplets, 66H, $P(C_6H_{11})_3$), d 2.29-2.41 (m, 3H, $P(C_6H_{11})_3$), d 2.60-2.72 (m, 3H, $P(C_6H_{11})_3$), d 17.45 (dd, 1H, Ru=CH, $^2J_{P-H}$=36.6 Hz, $^3J_{P-H}$=1.6 Hz). $^{31}P\{^1H\}$ NMR ($CD_2Cl_2$, 25° C.): d 56.3 (s, 1P, Ru=CH($PCy_3$)), d 88.7 (s, 1P, $Cy_3P$—Ru). $^{11}B\{^1H\}$ NMR ($CD_2Cl_2$, 25° C.): d-17.4.

EXAMPLE 7

Synthesis of [($H_2IMes$)$Cl_2$Ru=CH($PCy_3$)]$^+$[B($C_6F_5$)$_4$]$^-$ (3c)

Figure 4:
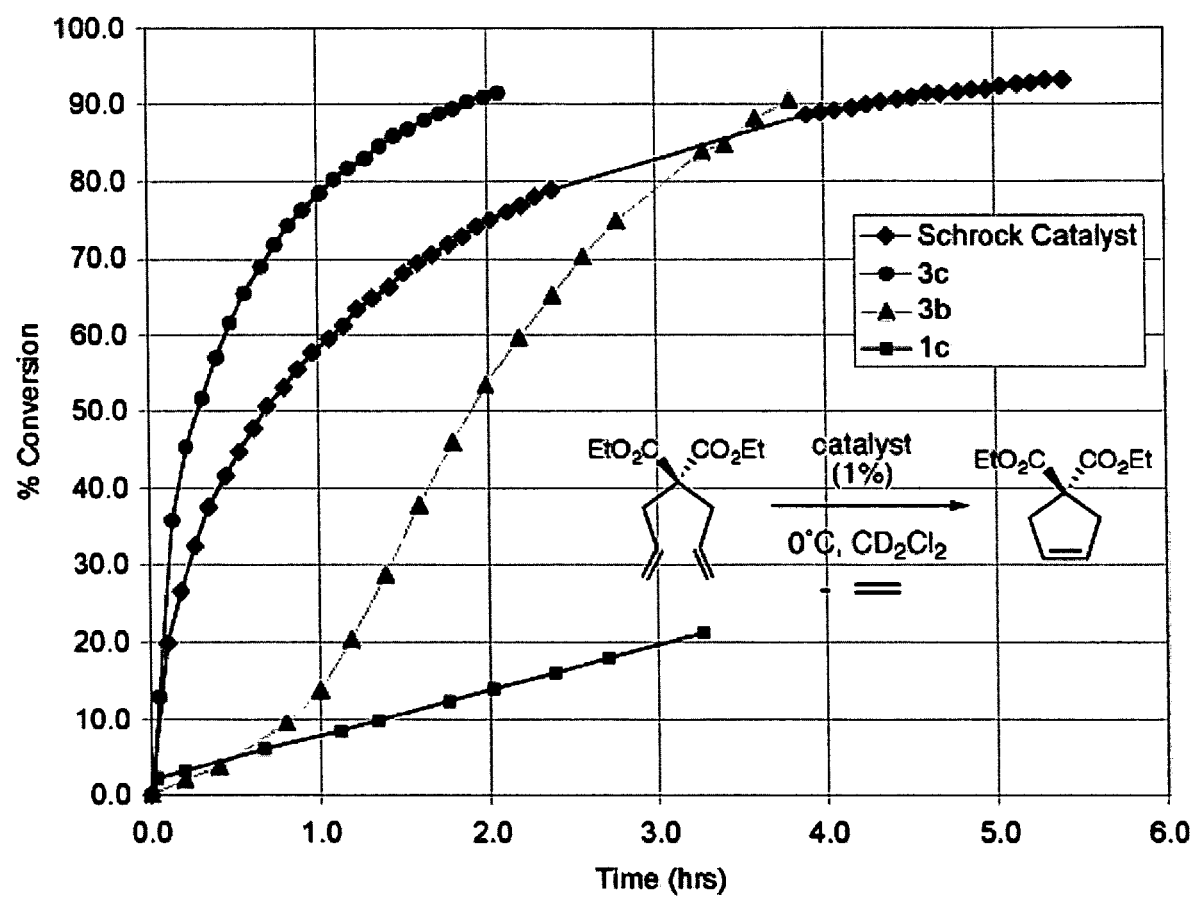
FIG. 4. illustrates in graph form the relative rates of conversion for the ring-closing metathesis of diethyldiallylmalonate at 273° K. catalyzed by prior art catalysts and an organometallic complex of the invention.

($H_2IMes$)($Cy_3P$)$Cl_2$Ru≡C (2c, 80 mg, 0.10 mmol) and [H($Et_2O$)$_2$]$^+$[B($C_6F_5$)$_4$]$^-$ (86 mg, 0.10 mmol) were placed into a 25 ml round bottom flask, which was fitted with a glass connector with a Kontes valve and attached to the vacuum line. The flask was evacuated and $CH_2Cl_2$ (10 ml) was vacuum transferred onto the solids at −78° C. The system was warmed to room temperature and stirred for 1 hour. The solvent was then removed under vacuum leaving a brown residue. Pentane (20 ml) was vacuum transferred onto the residue and the system was sonicated for 5 minutes, leaving a brown suspension. After allowing the solid to settle, the solvent was decanted via cannula, and the brown powder left was dried under full vacuum for 1 hour. Yield: 150 mg, 95%. $^1H$ NMR ($CD_2Cl_2$, 25° C.): d 1.26-1.11 (m, XH, $P(C_6H_{11})_3$), d 1.83 broad m, XH, $P(C_6H_{11})_3$), d 2.37 (s, 12H, o-$CH_3$-Mes),d 2.38 (s, 6H,p-$CH_3$-Mes), d 4.21 (s, 4H, $CH_2$-$CH_2$ bridge in IMes), d 7.01 (s, 4H, m-H-Mes), d 17.7 (d, 1H, Ru=CH). $^{31}P\{^1H\}$ NMR ($CD_2Cl_2$, 25° C.): d 54.05 (Ru=CH($PCy_3$)). $^{11}B\{^1H\}$ NMR ($CD_2Cl_2$, 25° C.): d-17.4. The structure of the compound in the solid state was determined by x-ray diffraction methods and is shown in FIG. 4 with selected bond lengths and angles. In FIG. 4, selected bond distances (Å) are as follows: Ru—C(1), 1.817(2); Ru—C(2), 1.988(2); Ru—Cl(1), 2.2951(5); Ru—Cl(2), 2.2809(5); P—C(1), 1.805(2). Selected bond angles (°): C(1)—Ru—C(2), 100.07(7); Cl(1)—Ru—Cl(2), 150.51(2); Cl(1)—Ru—C(1), 103.15(6); Cl(2)—Ru—C(1), 102.79(6); Cl(1)—Ru—C(2), 96.14(5); Cl(2)—Ru—C(2), 92.90(5). Selected torsion angle (°): C(2)—Ru—C(1)—P, −175.06(11).

EXAMPLE 8

Comparison of Relative Catalytic Activities in Ring-Closing Metathesis

Catalytic runs for the ring-closing metathesis of diethyldiallylmalonate were performed under standard conditions for each catalyst tested, using 1% mol catalyst loadings. The catalysts tested were complex 1c, complex 3b, complex 3c, ($H_2IMes$)$Cl_2$(3-Br-py)Ru=CHPh, and Schrock's molybdenum alkylidene, having the structure

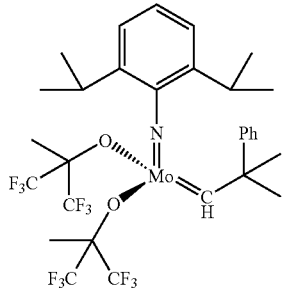

A stock solution of catalyst was prepared in the drybox by weighing 0.0025 mmol in a 1.0 ml graduated flask and dissolving in $CD_2Cl_2$. From this solution, 400 mL (0.001 mmol) were then transferred into an NMR tube, which was capped with a rubber septum and wrapped with parafilm. A separate $CD_2Cl_2$ diene stock solution was prepared by weighing 1.00 mmol into a 1 ml volumetric flask and refilling with $CD_2Cl_2$ to the marked level. 100 mL of this diene solution was taken up in a gastight syringe, and taken outside the drybox along with the NMR tube containing the dissolved catalyst. The tube was then immersed into a dry/ice acetone bath (−78° C.) and the diene solution was slowly injected through the rubber septum. The sample was shaken and introduced into the NMR probe which was precooled at 0° C. After allowing the sample to equilibrate, the progress of the reaction at 0° C. was monitored automatically at 3 to 10 minutes intervals depending on the catalyst, by measuring the disappearance of the methylene resonance of diethyldiallylmalonate versus product. FIG. 4 shows the relative rates of conversion for the RCM of diethyldiallylmalonate. The symbols used in the graph are as follows: ■—complex 1c; ▲—complex 3b; ●—complex 3c; ✹—($H_2IMes$)$Cl_2$(3-Br-py)Ru=CHPh; and ◆—Schrock's molybdenum alkylidene.

As may be deduced from FIG. 4, the electron-withdrawing nature of the phosphonium substituent in the carbene ligands of complexes 3b and 3c does not impede their ability to conduct olefin metathesis; they are exceptionally active RCM catalysts relative to catalyst precursor 1c. That is, catalyst precursor 1c is a poor initiator and only reached approximately 25% conversion after 4 hours. Complex 3b fared somewhat better, providing approximately 90% conversion after 4 hours, while Schrock's catalyst mediated the reaction to a similar point of progress over this time frame. The sigmoidal shape of the curve for 3b is reflective of the different activities of initiating versus propagating species at 0° C. for this catalyst; see Dias (1997), supra. The transformation was very rapid for complex 3c, however, which brought the reaction to >90% conversion after only 2 hours at 0° C., twice as fast as the Schrock catalyst under these conditions and, significantly, out-performing the rapidly initiating Grubbs catalyst incorporating the relatively labile 3-bromopyridine ligands. Furthermore, the rate of RCM for complex 3c is qualitatively similar to the best Blechert catalyst (Wakamatsu et al. (2002) *Angew. Chem.* 114:2509), a less conveniently available metathesis catalyst.

EXAMPLE 9

Synthesis of $[(H_2IMes)Cl_2Ru\!=\!CMe(PCy_3)]^+[BF_4]^-$ $(H_2IMes)(Cy_3P)Cl_2Ru\!\equiv\!C$: (2c, 80 mg, 0.10 mmol) and $[Me_3O]^+[BF_4]^-$ (15 mg, 0.10 mmol) are placed into a 25 ml round bottom flask, which is fitted with a glass connector with a Kontes valve and attached to the vacuum line. The flask is evacuated and $CH_2Cl_2$ (10 ml) is vacuum transferred onto the solids at −78° C. The system is warmed to room temperature and stirred for 1 hour. After removing the solvent under vacuum, pentane (20 ml) is vacuum transferred onto the residue and the mixture is sonicated, leaving a suspension. After decanting the solvent via cannula, the powder is dried under vacuum.

EXAMPLE 10

Synthesis of $[(H_2IMes)Cl_2Ru\!=\!CHCH_2(PPh_3)]^+[BF_4]^-$ $(H_2IMes)(PCy_3)Cl_2Ru\!=\!CHPh$ (1c, 85 mg, 0.10 mmol) and $[H_2C\!=\!CHCH_2PPh_3]^+[BF_4]^-$ (39 mg, 0.10 mmol) are placed into a 25 ml round bottom flask, which is fitted with a glass connector with a Kontes valve and attached to the vacuum line. The flask is evacuated and $CH_2Cl_2$ (10 ml) is vacuum transferred onto the solids at −78° C. The system is warmed to room temperature and stirred for 1 hour. After removing the solvent under vacuum, pentane (20 ml) is vacuum transferred onto the residue and the mixture is sonicated, leaving a suspension. The solvent is decanted and the solid washed with additional pentane until the washings are colorless. The resulting solid is dried under vacuum.

EXAMPLE 11

Synthesis of $[(H_2IMes)(py)Cl_2Ru\!=\!CHCH_2(PPh_3)]^+[BF_4]^-$ $(H_2IMes)(py)_2Cl_2Ru\!=\!CHPh$ (73 mg, 0.10 mmol) and $[H_2C\!=\!CHCH_2PPh_3]^+[BF_4]^-$ (39 mg, 0.10 mmol) are placed into a 25 ml round bottom flask, which is fitted with a glass connector with a Kontes valve and attached to the vacuum line. The flask is evacuated and $CH_2Cl_2$ (10 ml) is vacuum transferred onto the solids at −78° C. The system is warmed to room temperature and stirred for 4 hours. After removing the solvent under vacuum, pentane (20 ml) is vacuum transferred onto the residue and the mixture is sonicated, leaving a suspension. After decanting the solvent via cannula, the powder is dried under vacuum.

EXAMPLE 12

Synthesis of $[(H_2IMes)(py)Cl_2Ru\!=\!CH(PCy_3)]^+[BF_4]^-$ $[(H_2IMes)Cl_2Ru\!=\!CH(PCy_3)][BF_4]^-$ (3c, 86 mg, 0.10 mmol) is placed into a 25 ml round bottom flask, which is fitted with a glass connector with a Kontes valve and attached to the vacuum line. The flask is evacuated and $CH_2Cl_2$ (10 ml) is vacuum transferred onto the solids at −78° C. Excess pyridine (100 μl, 1.2 mmol) is added by syringe and the system is warmed to room temperature and stirred for 4 hours. After removing the solvent under vacuum, pentane (20 ml) is vacuum transferred onto the residue and the mixture is sonicated, leaving a suspension. After decanting the solvent via cannula, the powder is carefully dried under vacuum.

EXAMPLE 13

Alternative Synthesis and Purification of $(IH_2Mes)(PC_3)Cl2Ru\!\equiv\!C$: (2c)

In a glove box, $[(IH_2Mes)(PCy_3)Cl_2Ru\!=\!CHPh]$ (1.00 g, 1.18 mmol) was dissolved in $CH_2Cl_2$ (10 ml) and a solution of Feist's ester (200 mg, 1.18 mmol) in $CH_2Cl_2$ (5 ml) was added at room temperature. The reaction mixture was stirred at room temperature for 15 hours. Removal of volatiles under reduced pressure gave a waxy brown solid to which pentane (15 ml) was added and the mixture sonicated for 10 minutes. The pentane was removed via syringe and the pentane/sonication process repeated twice. The product was then dissolved in $CH_2Cl_2$ (5 ml) loaded onto a silica-plug (4×4 cm) and the plug flushed with a 1:1 mixture of hexane: ethyl acetate and the yellow fraction collected. The volatiles were removed under vacuum. The resulting sandy solid contains ethyl acetate of crystallization, however, repeating a process three times of dissolving the solid in $CH_2Cl_2$ (5 ml) and removing volatiles under reduced pressure removes all ethyl acetate. The resulting waxy brown solid was triturated with pentane (10 ml) to afford pure $[(IH_2Mes)(PCy_3)Cl_2RuC\!:\!]$ as a sandy solid (725 mg, 80%). This method of purification yields a product free of an unidentified small impurity, which causes complications in the isolation of pure $[(IH_2Mes)Cl_2Ru\!=\!CH(PCy_3)]^+[BF_4]^-$. Spectral features matched those previously reported; see Carlson (2002), cited supra.

EXAMPLE 14

Alternative Synthesis of $[(IH_2MeS)Cl_2Ru\!=\!CH(PCy_3)]^+[BF_4]^-$ $(IH_2MeS)(PCy_3)Cl_2Ru\!\equiv\!C$: (100 mg, 0.130 mmol) was dissolved in $CH_2Cl_2$ (10 ml) and cooled at −78° C. A solution of $HBF_4$ (0.174 M in $Et_2O$ 0.75 ml, 0.130 mmol) was added dropwise. The reaction mixture was allowed to warm at room temperature and stirred for 2 hrs. Removal of volatiles under reduced pressure gave a dark waxy brown solid to which pentane (10 ml) was added and the mixture sonicated for 10 minutes. The pentane was removed via syringe to afford a brown solid. The solid thus obtained contains a small quantity (<5%) of unreacted starting material. Recrystallization from dichloromethane/pentane at −30° C. afforded pure (as judged by $^1H$ NMR spectroscopy) $[(IH_2Mes)Cl_2Ru\!=\!CH(PCy_3)]^+[BF_4]^-$ (89 mg, 80%).

EXAMPLE 15

Synthesis of $[(IH_2Mes)Cl_2Ru\!=\!CH(PCy_3)]^+[OTf]^-$ $[(IH_2Mes)(PCy_3)Cl_2Ru\!\equiv\!C\!:\!]$ (200 mg, 0.259 mmol) was weighed into a 50 ml round bottom flask and dissolved in 5 ml of $CH_2Cl_2$. To this solution 38.9 mg (0.259 mmol) of triflic acid, also dissolved in 5 ml of $CH_2Cl_2$, was added at once. An immediate change in color from yellow to dark brown was observed. The solution was stirred for 30 minutes and the solvent was removed under vacuum, leaving a tan solid. The solid was suspended in pentane (15 ml), stirred for 10 minutes, the solvent decanted via cannula and the product was then dried under vacuum. The yield was quantitative. Spectral features are identical to those reported for $[(IH_2Mes)Cl_2Ru\!=\!CH(PCy_3)]^+[B(C_6F_5)_4]^-$, except for those corresponding to the new counteranion: $^{19}F$ NMR $(CD_2Cl_2, 25° C.)$: δ-79.0 (s, $CF_3SO_3^-$).

EXAMPLE 16

Synthesis of [(IH$_2$Mes)Cl$_2$Ru=CH(PCy$_3$)]$^+$[BPh$_4$]$^-$

[(IH$_2$Mes)(PCy$_3$)Cl$_2$Ru≡C:] (500 mg, 0.648 mol) was dissolved in 15 ml of CH$_2$Cl$_2$ in a 50 ml round bottom flask, and then 97.2 mg (0.648 mmol) of triflic acid also dissolved in CH$_2$Cl$_2$ (5 ml) was added at once. The reaction mixture was stirred at room temperature for 45 minutes and then, solid NaBPh$_4$ was added at once to the brown solution. The suspension was stirred for 1 hr at room temperature and was then cooled at –35° C. in the freezer overnight, to induce total precipitation of the NaOTf by product. The mixture was then filtered through Celite and the solvent evaporated, leaving a tan powder. $^1$H and $^{31}$P{$^1$H} NMR spectra of several batches showed this crude mixture to be pure and no further manipulations were necessary. Spectral features are identical to those reported for [(IH$_2$Mes)Cl$_2$Ru=CH(PCy$_3$)]$^+$ [B(C$_6$F$_5$)$_4$]$^-$, except for those corresponding to the new couteranion: $^1$H NMR (400 MHz, CD$_2$Cl$_2$, 25° C.): δ7.30 (broad, o-C$_6$H$_5$B), 6.99 (t, m-C$_6$H$_5$B), 6.86 (t,p-C$_6$H$_5$B). $^{11}$B NMR (CD$_2$Cl$_2$, 25° C.): δ-7.23 (s, C$_6$H$_5$B).

EXAMPLE 17

Confirmation of Structures by X-Ray Diffraction

Figure 3:
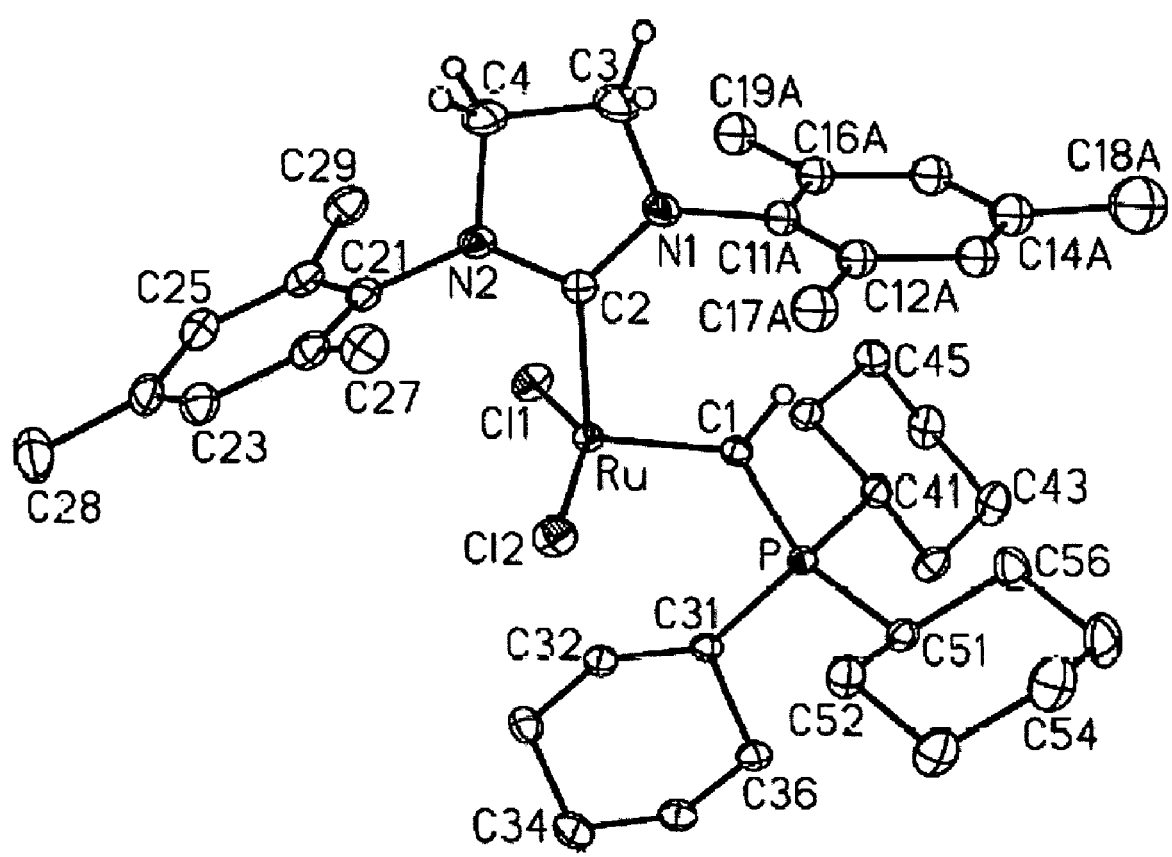
FIG. 3 provides the ORTEP diagram of the X-ray crystal structure of $(H_2IMes)(PCy_3)Ru=CH(PCy_3)^+[B(C_6F_5)]^-$, synthesized as described in Example 7.
Figure 5:
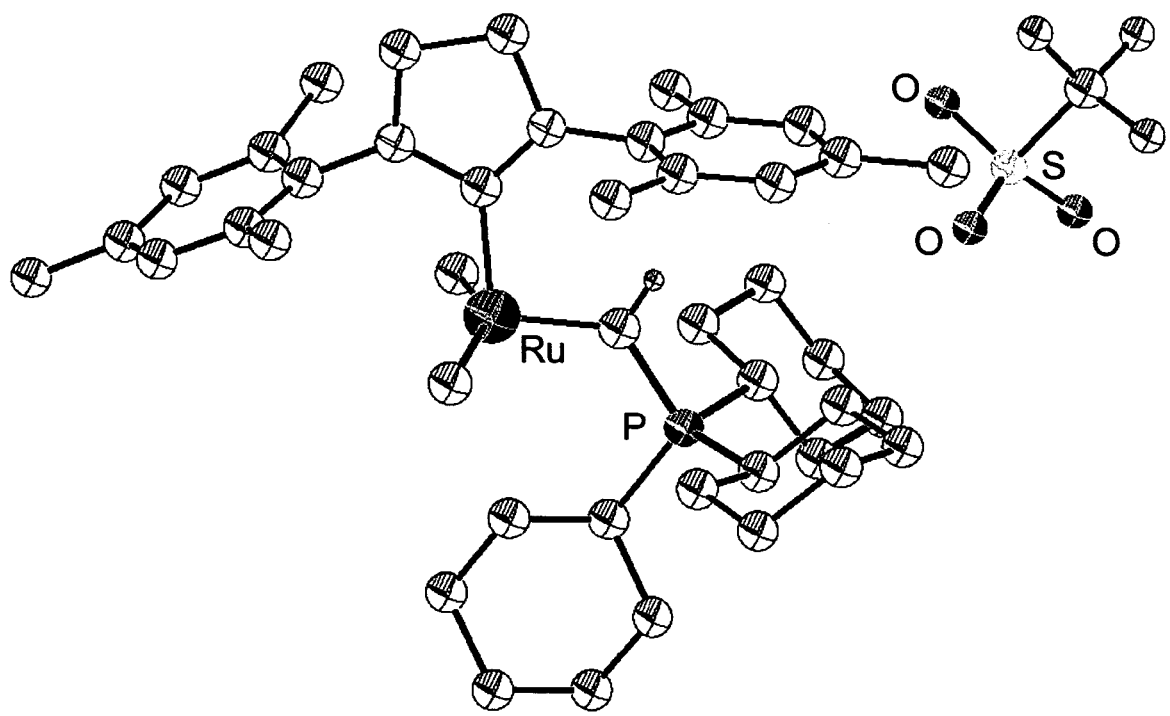
FIG. 5 provides the ORTEP diagram of the X-ray crystal structure of $[(IH_2Mes)Cl_2Ru=CH(PCy_3)]^+[OTf]^-$, synthesized as described in Example 15.
Figure 6:
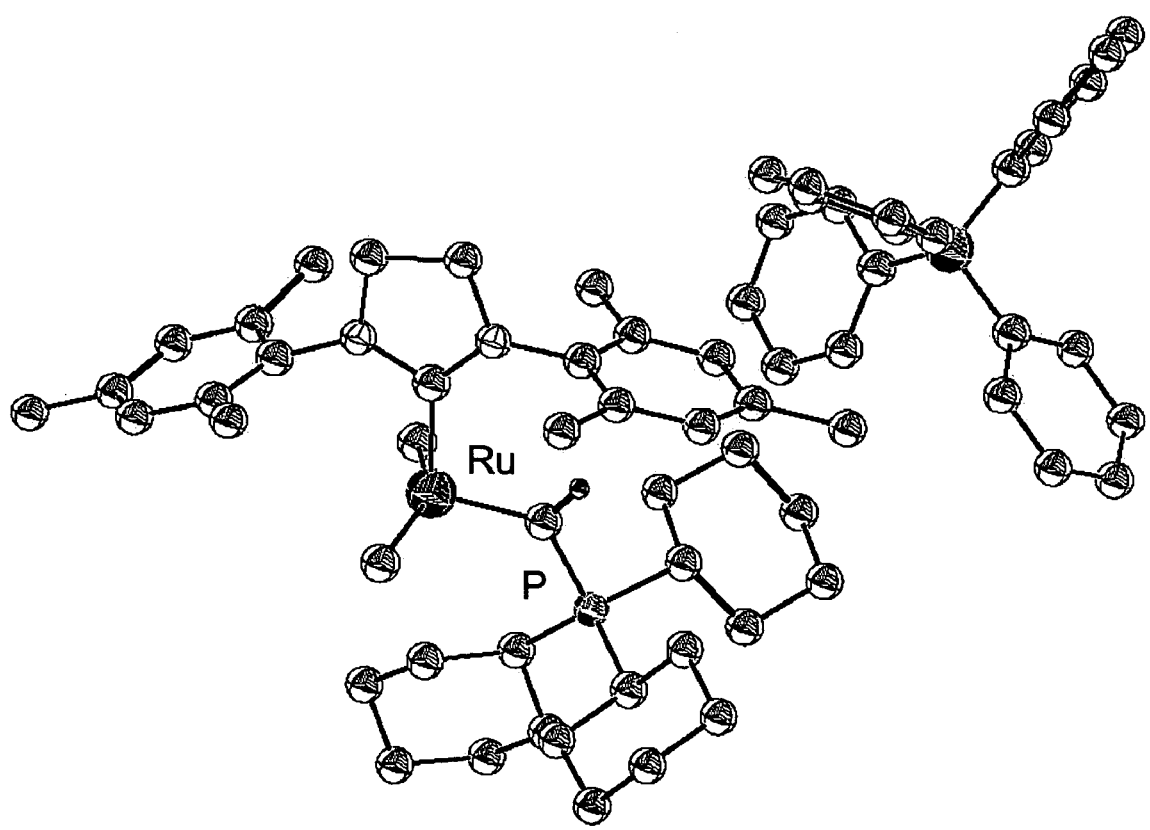
FIG. 6 provides the ORTEP diagram of the X-ray crystal structure of $[(IH_2Mes)Cl_2Ru=CH(PCy_3)]^+[BPh_4]^-$, synthesized as described in Example 16.

The structures of the compounds prepared in Examples 15 and 16 in the solid state were determined by x-ray diffraction methods and are shown in FIGS. 5 and 6, respectively, with selected bond lengths and angles. In both cases, no close contact between the counteranion and the ruthenium center were observed; all distances were greater than 6.99 Å for [(IH$_2$Mes)Cl$_2$Ru=CH(PCy$_3$)]$^+$[OTf]$^-$ (FIG. 5) and greater than 7.83 Å for [(IH$_2$Mes)Cl$_2$Ru=CH(PCy$_3$)]$^+$[BPh$_4$]$^-$ (FIG. 6). Distances and angles in the cationic ruthenium portion are identical (within experimental error) to those reported for [(IH$_2$Mes)Cl$_2$Ru=CH(PCy$_3$)]$^+$[B(C$_6$F$_5$)$_4$]$^-$ (see Example 7 and FIG. 3).

We claim:

1. An organometallic complex having the structure of formula (I)

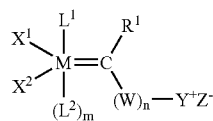

(I)

wherein:

M is a Group 8 transition metal;
L$^1$ and L$^2$ are neutral electron donor ligands;
X$^1$ and X$^2$ are anionic ligands;
R$^1$ is hydrogen, C$_1$-C$_{12}$ hydrocarbyl, or substituted C$_1$-C$_{12}$ hydrocarbyl;
W is an optionally substituted and/or optionally heteroatom-containing C$_1$-C$_{20}$ hydrocarbylene linkage;
Y is a positively charged Group 15 or Group 16 element substituted with hydrogen, C$_1$-C$_{12}$ hydrocarbyl, substituted C$_1$-C$_{12}$ hydrocarbyl, heteroatom-containing C$_1$-C$_{12}$ hydrocarbyl, or substituted heteroatom-containing C$_1$-C$_{12}$ hydrocarbyl;
Z$^-$ is a negatively charged counterion;
m is zero or 1; and
n is zero or 1;

wherein any two or more of L$^1$, L$^2$, X$^1$, X$^2$, R$^1$, W, and Y can be taken together to form a cyclic group.

2. The complex of claim 1, wherein M is Ru or Os.
3. The complex of claim 2, wherein M is Ru.
4. The complex of claim 3, wherein R$^1$ is hydrogen or C$_1$-C$_{12}$ alkyl.
5. The complex of claim 4, wherein R$^1$ is hydrogen.
6. The complex of claim 1, wherein m and n are zero, such that the complex has the structure of formula (II)

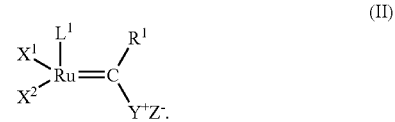

(II)

7. The complex of claim 6, wherein Y is selected from P(R$^2$)$_3$, N(R$^2$)$_3$, As(R$^2$)$_3$, S(R$^2$)$_2$, O(R$^2$)$_2$, where the R$^2$ are independently selected from C$_1$-C$_{12}$ hydrocarbyl.
8. The complex of claim 7, wherein Y is P(R$^2$)$_3$.
9. The complex of claim 8, wherein the R$^2$ are independently selected from C$_1$-C$_{12}$ alkyl and aryl.
10. The complex of claim 9, wherein the R$^2$ are independently selected from methyl, ethyl, n-propyl, isopropyl, n-butyl, isobutyl, t-butyl, cyclopentyl, cyclohexyl, and phenyl.
11. The complex of claim 6, wherein Y is selected from optionally substituted pyridinyl, pyrazinyl, and imidazolyl.
12. The complex of claim 6, wherein L$^1$ is selected from phosphine, sulfonated phosphine, phosphite, phosphinite, phosphonite, arsine, stilbine, ether, amine, amide, imine, sulfoxide, carboxyl, nitrosyl, pyridine, substituted pyridine, imidazole, substituted imidazole, pyrazine, thioether, and heteroatom-substituted carbene.
13. The complex of claim 12, wherein L$^1$ is a phosphine of the formula PR$^5$R$^6$R$^7$, where R$^5$, R$^6$, and R$^7$ are each independently aryl or C$_1$-C$_{12}$ alkyl.
14. The complex of claim 13, wherein L$^1$ is selected from tricyclohexylphosphine, tricyclopentylphosphine, triisopropylphosphine, triphenylphosphine, diphenylmethylphosphine, and phenyldimethylphosphine.
15. The complex of claim 6, wherein L$^1$ has the structure of formula (III)

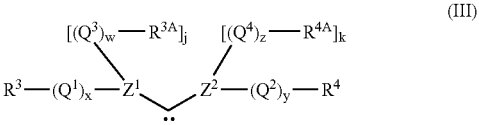

(III)

wherein:

Z$^1$ and Z$^2$ are heteroatoms selected from N, O, S, and P;
j is zero when Z$^1$ is O or S, and j is 1 when Z$^1$ is N or P;
k is zero when Z$^2$ is O or S, and k is 1 when Y$^1$ is N or P;
Q$^1$, Q$^2$, Q$^3$, and Q$^4$ are independently selected from C$_1$-C$_{12}$ hydrocarbylene, substituted C$_1$-C$_{12}$ hydrocarbylene, heteroatom-containing C$_1$-C$_{12}$ hydrocarbylene, substituted heteroatom-containing C$_1$-C$_{12}$ hydrocarbylene, and —(CO)—;
w, x, y, and z are independently zero or 1; and
R$^3$, R$^{3A}$, R$^4$, and R$^{4A}$ are independently selected from hydrogen, C$_1$-C$_{20}$ hydrocarbyl, substituted C$_1$-C$_{20}$ hydrocarbyl, heteroatom-containing $C_1$-$C_{20}$ hydrocarbyl, and substituted heteroatom-containing $C_1$-$C_{20}$ hydrocarbyl, such that the complex is a ruthenium carbene complex having the structure of formula (IV)

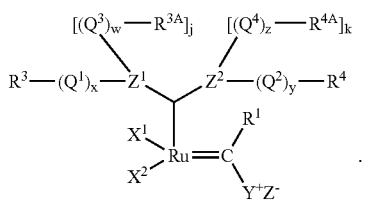

(IV)

16. The complex of claim 15, wherein w, x, y, and z are zero, $Z^1$ and $Z^1$ are N, and $R^{3A}$ and $R^{4A}$ are linked to form —Q—, such that the complex has the structure of formula (V)

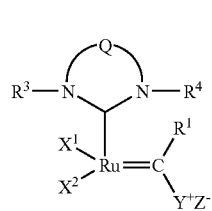

(V)

wherein Q is a $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, and further wherein two or more substituents on adjacent atoms within Q may be linked to form an additional cyclic group.

17. The complex of claim 16, wherein Q has the structure —$CR^8R^9$—$CR^{10}R^{11}$— or —$CR^8$=$CR^{10}$—, wherein $R^8$, $R^9$, $R^{10}$, and $R^{11}$ are independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups, and wherein any two of $R^8$, $R^9$, $R^{10}$, and $R^{11}$ may be linked together to form a substituted or unsubstituted, saturated or unsaturated ring.

18. The complex of claim 17, wherein Q has the structure —$CR^8R^9$—$CR^{10}R^{11}$—, and $R^8$, $R^9$, $R^{10}$, and $R^{11}$ are hydrogen.

19. The complex of claim 17, wherein Q has the structure —$CR^8$=$CR^{10}$—, and $R^8$ and $R^{10}$ are hydrogen.

20. The complex of claim 17, wherein $R^3$ and $R^4$ are aromatic, substituted aromatic, heteroaromatic, substituted heteroaromatic, alicyclic, substituted alicyclic, heteroatom-containing alicyclic, or substituted heteroatom-containing alicyclic, composed of from one to about five rings.

21. The complex of claim 20, wherein $R^3$ and $R^4$ are the same and are either aromatic or $C_7$-$C_{12}$ alicyclic, if aromatic, each having the structure of formula (VI)

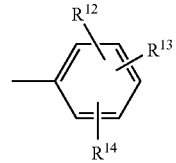

(VI)

in which $R^{12}$, $R^{13}$, and $R^{14}$ are each independently hydrogen, $C_1$-$C_{12}$ alkyl, $C_1$-$C_{12}$ alkoxy, $C_5$-$C_{14}$ aryl, substituted $C_5$-$C_{14}$ aryl, or halide.

22. The complex of claim 21, wherein $R^3$ and $R^4$ are mesityl.

23. The complex of claim 6, wherein $X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and phenyl.

24. The complex of claim 23, wherein $X^1$ and $X^2$ are selected from halide, mesylate, tosylate, fluorinated $C_2$-$C_{20}$ acyloxy, fluorinated $C_1$-$C_{20}$ alkylsulfonate, fluorinated $C_1$-$C_{20}$ alkoxy, and fluorinated $C_5$-$C_{20}$ aryloxy.

25. The complex of claim 24, wherein $X^1$ and $X^2$ are chloro.

26. The complex of claim 6, wherein $[Z]^-$ is selected from $[B(C_6F_5)_4]^-$, $[BF_4]^-$, $[B(C_6H_6)_4]^-$, $[CF_3S(O)_3]^-$, $[PF_6]^-$, $[SbF_6]^-$, and $[AlCl_4]^-$ $[FSO_3]^-$, $[CB_{11}H_6Cl_6]^-$, $[CB_{11}H_6Br_6]^-$, and $[SO_3F:SbF_5]^-$.

27. The complex of claim 26, wherein $Z^-$ is of the formula $B(R^{15})_4^-$ where $R^{15}$ is fluoro, aryl, or perfluorinated aryl.

28. The complex of claim 27, wherein $R^{15}$ is fluoro or perfluorinated aryl.

29. The complex of claim 6, wherein:
$L^1$ is 1,3-dimesitylimidazole-2-ylidene (IMes) or 1,3-dimesityl-4,5-dihydroimidazol-2-ylidene ($H_2$IMes);
$X^1$ and $X^2$ are chloro;
Y is $P(R^2)_3$, wherein the $R^2$ are independently selected from $C_1$-$C_6$ alkyl and phenyl; and
$Z^-$ is $BF_4^-$ or $B(C_6F_5)^-$.

30. The complex of claim 1, wherein m is 1 and n is 1, such that the complex has the structure of formula (VII)

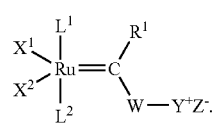

(VII)

31. The complex of claim 30, wherein W is an optionally substituted $C_1$-$C_{12}$ alkylene linkage.

32. The complex of claim 31, wherein $L^1$ is selected from phosphine, sulfonated phosphine, phosphite, phosphinite, phosphonite, arsine, stilbine, ether, amine, amide, imine, sulfoxide, carboxyl, nitrosyl, pyridine, substituted pyridine, imidazole, substituted imidazole, pyrazine, thioether, and heteroatom-substituted carbene, and $L^2$ is selected from phosphine, sulfonated phosphine, phosphite, phosphinite, phosphonite, arsine, stilbine, ether, amine, amide, imine, sulfoxide, carboxyl, nitrosyl, pyridine, substituted pyridine, imidazole, substituted imidazole, pyrazine, and thioether.

33. The complex of claim 32, wherein $L^1$ is N-heterocyclic carbene ligand.

34. The complex of claim 33, wherein $L^2$ is a phosphine ligand.

35. The complex of claim 34, wherein $L^2$ is of the formula $PR^5R^6R^7$, where $R^5$, $R^6$, and $R^7$ are each independently aryl or $C_1$-$C_{12}$ alkyl.

36. The complex of claim 35, wherein:
$L^1$ is 1,3-dimesitylimidazole-2-ylidene (IMes) or 1,3-dimesityl-4,5-dihydroimidazol-2-ylidene ($H_2$IMes);
$L^2$ is selected from tricyclohexylphosphine, tricyclopentylphosphine, triisopropylphosphine, triphenylphosphine, diphenylmethylphosphine, and phenyldimethylphosphine;
W is an optionally substituted $C_1$-$C_{12}$ alkylene linkage;
$X^1$ and $X^2$ are chloro;
Y is $P(R^2)_3$, wherein the $R^2$ are independently selected from $C_1$-$C_6$ alkyl and phenyl; and
$Z^-$ is $BF_4^-$ or $B(C_6F_5)^-$.

37. A method for synthesizing an organometallic complex having the structure of formula (XI)

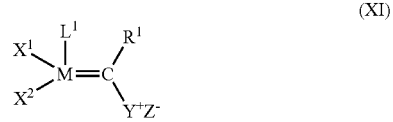

(XI)

wherein M is a Group 8 transition metal, $L^1$ is a neutral electron donor ligand, $X^1$ and $X^2$ are anionic ligands, $R^1$ is hydrogen, $C_1$-$C_{12}$ hydrocarbyl, or substituted $C_1$-$C_{12}$ hydrocarbyl, Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, and $Z^-$ is a negatively charged ion, the method comprising:
contacting a Group 8 transition metal carbide having the structure $(X^1X^2)(L^1Y)M\equiv C$: with an ionic reagent of the formula $[R^1]^+[Z]^-$.

38. The method of claim 37, wherein M is Ru or Os.

39. The method of claim 38, wherein M is Ru.

40. The method of claim 39, wherein the $[R^1]^+$ moiety in the ionic reagent is associated with a polar solvent.

41. The method of claim 40, wherein $R^1$ is hydrogen.

42. The method of claim 41, wherein $[Z]^-$ is selected from $[B(C_6F_5)_4]^-$, $[BF_4]^-$, $[B(C_6H_6)_4]^-$, $[CF_3S(O)_3]^-$, $[PF_6]^-$, $[SbF_6]^-$, and $[AlCl_4]^-$ $[FSO_3]^-$, $[CB_{11}H_6Cl_6]^-$, $[CB_{11}H_6Br_6]^-$, and $[SO_3F{:}SbF_5]^-$.

43. A method for synthesizing an organometallic complex having the structure of formula (II)

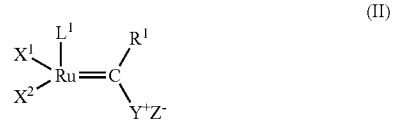

(II)

wherein $L^1$ is a neutral electron donor ligand, $X^1$ and $X^2$ are anionic ligands, $R^1$ is hydrogen, Y is a $C_1$-$C_{12}$ hydrocarbyl-substituted, positively charged Group 15 or Group 16 element, and $Z^-$ is of the formula $B(R^{15})_4^-$ where $R^{15}$ is fluoro, aryl, or perfluorinated aryl, the method comprising:

(a) contacting (i) a ruthenium complex having the structure $(X^1X^2)(L^1Y)Ru=CHR^{16}$ where $R^{16}$ is $C_1$-$C_{20}$ hydrocarbyl with (ii) a reagent effective to convert the ruthenium complex to the ruthenium carbide $(X^1X^2)(Y)Ru\equiv C$:; and (b) contacting the ruthenium carbide with a protonating reagent of the formula $[H(OR_2)_2]^+[B(R^{15})_4]^-$ where R is $C_1$-$C_6$ hydrocarbyl.

44. A method for synthesizing an organometallic complex having the structure of formula (XII)

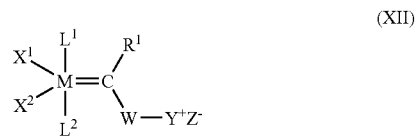

(XII)

wherein M is a Group 8 transition metal, $L^1$ and $L^2$ are neutral electron donor ligands, $X^1$ and $X^2$ are anionic ligands, $R^1$ is hydrogen, $C_1$-$C_{12}$ hydrocarbyl, or substituted $C_1$-$C_{12}$ hydrocarbyl, W is an optionally substituted and/or optionally heteroatom-containing $C_1$-$C_{20}$ hydrocarbylene linkage, Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl, and $Z^-$ is a negatively charged ion, the method comprising:
contacting an organometallic complex having the structure $(X^1X^2)(L^1L^2)M=CHR^{16}$ where $R^{16}$ is $C_1$-$C_{20}$ hydrocarbyl with an ionic reagent having the structure $H_2C=CR^1-W-Y^+Z^-$ under conditions effective to enable cross metathesis between the transition metal alkylidene group in the complex and the olefinic moiety in the reagent.

45. A method for synthesizing an organometallic complex having the structure of formula (VII)

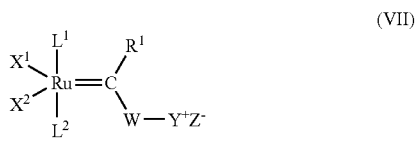

(VII)

wherein $L^1$ and $L^2$ are neutral electron donor ligands, $X^1$ and $X^2$ are anionic ligands, $R^1$ is hydrogen, $C_1$-$C_{12}$ hydrocarbyl, or substituted $C_1$-$C_{12}$ hydrocarbyl, W is an optionally substituted $C_1$-$C_{12}$ alkylene linkage, Y is a $C_1$-$C_{12}$ hydrocarbyl-substituted, positively charged Group 15 or Group 16 element, and $Z^-$ is of the formula $B(R^{15})_4^-$ where $R^{15}$ is fluoro, aryl, or perfluorinated aryl, the method comprising:
contacting a ruthenium complex having the structure $(X^1X^2)(L^1L^2)Ru=CHR^{16}$ where $R^{16}$ is $C_1$-$C_{20}$ hydrocarbyl with an ionic reagent having the structure $H_2C=CR^1-W-Y^+Z^-$ under conditions effective to enable cross metathesis between the ruthenium alkylidene group in the complex and the olefinic moiety in the reagent.

46. A method for catalyzing an olefin metathesis reaction, comprising contacting an olefinic reactant with a catalytically effective amount of the complex of any one of claims 1, 6, 29, 30, and 36 under reaction conditions effective to enable olefin metathesis.

47. The method of claim 46, wherein the olefinic reactant is cyclic and the metathesis reaction is ring-opening metathesis polymerization (ROMP).

48. The method of claim 46, wherein the olefinic reactant is an acyclic diene, and the metathesis reaction is ring-closing metathesis (RCM) or acyclic diene metathesis (ADMET).

49. The method of claim 46, wherein two olefinic reactants are contacted with a catalytically effective amount of the complex, and the metathesis reaction is cross-metathesis.

* * * * *